US010327929B2

(12) United States Patent
Syed

(10) Patent No.: US 10,327,929 B2
(45) Date of Patent: Jun. 25, 2019

(54) APPARATUS AND METHOD FOR STABILIZATION OF PROCEDURAL CATHETER IN TORTUOUS VESSELS

(71) Applicant: RAM MEDICAL INNOVATIONS, LLC, Springfield, OH (US)

(72) Inventor: Mubin I. Syed, Springfield, OH (US)

(73) Assignee: RAM MEDICAL INNOVATIONS, LLC, Springfield, OH (US)

( * ) Notice: Subject to any disclaimer, the term of this patent is extended or adjusted under 35 U.S.C. 154(b) by 68 days.

(21) Appl. No.: 15/227,189

(22) Filed: Aug. 3, 2016

(65) Prior Publication Data
US 2017/0119563 A1 May 4, 2017

Related U.S. Application Data

(63) Continuation-in-part of application No. 14/929,030, filed on Oct. 30, 2015, now Pat. No. 9,980,838.
(Continued)

(51) Int. Cl.
*A61F 2/954* (2013.01)
*A61F 2/962* (2013.01)
(Continued)

(52) U.S. Cl.
CPC .............. *A61F 2/954* (2013.01); *A61B 17/00* (2013.01); *A61B 34/20* (2016.02); *A61F 2/962* (2013.01);
(Continued)

(58) Field of Classification Search
CPC ......... A61F 2/954; A61F 2/962; A61M 25/01; A61M 25/0043; A61B 34/20
See application file for complete search history.

(56) References Cited

U.S. PATENT DOCUMENTS 4,243,040 A 1/1981 Beecher
4,790,331 A 12/1988 Okada et al.
(Continued)

FOREIGN PATENT DOCUMENTS

CN 108472124 A 8/2018
CN 108472472 A 8/2018
(Continued)

OTHER PUBLICATIONS

International Search Report / Written Opinion issued in Int'l Application No. PCT/US2013/071271 dated Feb. 10, 2014, 7 pages.
(Continued)

*Primary Examiner* — Tuan V Nguyen
(74) *Attorney, Agent, or Firm* — Jennifer Hayes; Nixon Peabody LLP

(57) ABSTRACT

The use of bifurcated catheter is disclosed for stabilizing working catheters for carotid percutaneous intervention of vessels originating from a tortuous aortic arch, which uses guide wires that used to enable the catheters accessing the left or right carotid arteries (CA). Also disclosed is the use of two independent catheters or a catheter and snare wire within a single sheath, as well as the implementations, associated problems and corrective solutions to the identified problems. Further additional uses of the bifurcated catheter/dual catheter, for access to and treatment of other exemplary tortuous locations where stability of the procedural catheter would make a difference are also disclosed in the current application.

14 Claims, 25 Drawing Sheets

Related U.S. Application Data

(60) Provisional application No. 62/352,353, filed on Jun. 20, 2016.

(51) Int. Cl.
*A61B 34/20* (2016.01)
*A61M 25/00* (2006.01)
*A61M 25/01* (2006.01)
*A61B 17/00* (2006.01)
*A61M 25/09* (2006.01)
*A61M 25/10* (2013.01)

(52) U.S. Cl.
CPC ........ *A61M 25/0043* (2013.01); *A61M 25/01* (2013.01); *A61B 2017/00358* (2013.01); *A61B 2017/00477* (2013.01); *A61B 2017/00876* (2013.01); *A61M 25/09041* (2013.01); *A61M 2025/1045* (2013.01)

(56) References Cited

U.S. PATENT DOCUMENTS

| | | | |
|---|---|---|---|
| 5,098,707 A | 3/1992 | Baldwin et al. | |
| 5,293,772 A | 9/1994 | Carr, Jr. | |
| 5,344,426 A | 9/1994 | Lau et al. | |
| 5,419,777 A | 5/1995 | Hofling | |
| 5,571,135 A | 11/1996 | Fraser et al. | |
| 5,651,366 A | 7/1997 | Liang et al. | |
| 5,662,703 A | 9/1997 | Yurek et al. | |
| 5,669,924 A | 9/1997 | Shaknovich | |
| 5,690,644 A | 11/1997 | Yurek et al. | |
| 5,718,702 A | 2/1998 | Edwards | |
| 5,720,735 A | 2/1998 | Dorros | |
| 5,766,192 A | 6/1998 | Zacca | |
| 5,807,330 A | 9/1998 | Teitelbaum | |
| 5,813,976 A | 9/1998 | Filipi et al. | |
| 5,957,901 A | 9/1999 | Mottola et al. | |
| 5,997,563 A | 12/1999 | Kretzers | |
| 6,027,462 A | 2/2000 | Greene et al. | |
| 6,059,813 A | 5/2000 | Vrba et al. | |
| 6,070,589 A * | 6/2000 | Keith | A61F 2/07 128/898 |
| 6,152,141 A | 11/2000 | Stevens et al. | |
| 6,238,410 B1 | 5/2001 | Vrba et al. | |
| 6,245,017 B1 | 6/2001 | Hashimoto | |
| 6,245,573 B1 | 6/2001 | Spillert | |
| 6,428,567 B2 | 8/2002 | Wilson et al. | |
| 6,450,964 B1 | 9/2002 | Webler | |
| 6,464,665 B1 | 10/2002 | Heuser | |
| 6,494,875 B1 | 12/2002 | Mauch | |
| 6,544,278 B1 | 4/2003 | Vrba et al. | |
| 6,663,613 B1 | 12/2003 | Lewis et al. | |
| 6,764,505 B1 | 7/2004 | Hossainy et al. | |
| 6,780,174 B2 | 8/2004 | Mauch | |
| 6,808,520 B1 | 10/2004 | Fouirkas et al. | |
| 6,837,881 B1 | 1/2005 | Barbut | |
| 6,929,633 B2 | 8/2005 | Evans et al. | |
| 6,932,829 B2 | 8/2005 | Majercak | |
| 6,942,682 B2 | 9/2005 | Vrba et al. | |
| 7,235,083 B1 * | 6/2007 | Perez | A61F 2/954 604/164.09 |
| 7,393,358 B2 | 7/2008 | Malewicz | |
| 7,651,520 B2 | 1/2010 | Fischell et al. | |
| 7,674,493 B2 | 3/2010 | Hossainy et al. | |
| 7,740,791 B2 | 6/2010 | Kleine et al. | |
| 7,758,624 B2 | 7/2010 | Dorn et al. | |
| 7,763,010 B2 | 7/2010 | Evans et al. | |
| 7,766,961 B2 | 8/2010 | Patel et al. | |
| 7,828,832 B2 | 11/2010 | Belluche et al. | |
| 7,842,026 B2 | 11/2010 | Cahill et al. | |
| 7,955,370 B2 | 6/2011 | Gunderson | |
| 8,092,509 B2 | 1/2012 | Dorn et al. | |
| 8,119,184 B2 | 2/2012 | Hossainy et al. | |
| 8,202,309 B2 | 6/2012 | Styrc | |
| 8,241,241 B2 | 8/2012 | Evans et al. | |
| 8,343,181 B2 | 1/2013 | Duffy et al. | |
| 8,419,767 B2 | 4/2013 | Al-Qbandi et al. | |
| 8,535,290 B2 | 9/2013 | Evans et al. | |
| 8,721,714 B2 | 5/2014 | Kelley | |
| 8,727,988 B2 | 5/2014 | Flaherty et al. | |
| 8,728,144 B2 | 5/2014 | Fearnot | |
| 8,740,971 B2 | 6/2014 | Iannelli | |
| 8,986,241 B2 | 3/2015 | Evans et al. | |
| 8,998,894 B2 | 4/2015 | Mauch et al. | |
| 9,301,830 B2 | 4/2016 | Heuser et al. | |
| 9,314,499 B2 | 4/2016 | Wang et al. | |
| 9,636,244 B2 | 5/2017 | Syed | |
| 9,855,705 B2 | 1/2018 | Wang et al. | |
| 9,980,838 B2 | 5/2018 | Syed | |
| 2001/0003985 A1 | 6/2001 | Lafontaine et al. | |
| 2001/0049534 A1 | 12/2001 | Lachat | |
| 2002/0077691 A1 | 6/2002 | Nachtigall | |
| 2002/0123698 A1 | 9/2002 | Garibotto et al. | |
| 2002/0156518 A1 | 10/2002 | Tehrani | |
| 2002/0165535 A1 | 11/2002 | Lesh | |
| 2003/0088187 A1 | 5/2003 | Saadat et al. | |
| 2003/0216721 A1 | 11/2003 | Diederich | |
| 2003/0229282 A1 | 12/2003 | Burdette | |
| 2004/0073190 A1 | 4/2004 | Deem et al. | |
| 2004/0138734 A1 * | 7/2004 | Chobotov | A61F 2/954 623/1.11 |
| 2004/0147837 A1 | 7/2004 | Macaulay et al. | |
| 2005/0043779 A1 | 2/2005 | Wilson | |
| 2005/0101968 A1 | 5/2005 | Dadourian | |
| 2005/0113862 A1 | 5/2005 | Besselink et al. | |
| 2005/0222488 A1 | 10/2005 | Chang et al. | |
| 2005/0234499 A1 | 10/2005 | Olson et al. | |
| 2005/0251160 A1 | 11/2005 | Saadat et al. | |
| 2006/0025752 A1 | 2/2006 | Broaddus et al. | |
| 2006/0025844 A1 | 2/2006 | Majercak et al. | |
| 2006/0030923 A1 | 2/2006 | Gunderson | |
| 2006/0155363 A1 | 7/2006 | Laduca et al. | |
| 2006/0200221 A1 | 9/2006 | Malewicz | |
| 2006/0257389 A1 | 11/2006 | Binford | |
| 2006/0259063 A1 | 11/2006 | Bates et al. | |
| 2006/0270900 A1 | 11/2006 | Chin et al. | |
| 2007/0016019 A1 | 1/2007 | Salgo | |
| 2007/0016062 A1 | 1/2007 | Park | |
| 2007/0038061 A1 | 2/2007 | Huennekens et al. | |
| 2007/0038293 A1 | 2/2007 | St. Goar et al. | |
| 2007/0049867 A1 | 3/2007 | Shindelman | |
| 2007/0083215 A1 * | 4/2007 | Hamer | A61F 2/954 606/108 |
| 2007/0118151 A1 | 5/2007 | Davidson et al. | |
| 2007/0129719 A1 | 6/2007 | Kendale et al. | |
| 2008/0039746 A1 | 2/2008 | Hissong et al. | |
| 2008/0114239 A1 | 5/2008 | Randall et al. | |
| 2008/0194993 A1 | 8/2008 | McLaren et al. | |
| 2008/0208309 A1 | 8/2008 | Saeed | |
| 2008/0281398 A1 | 11/2008 | Koss | |
| 2009/0005679 A1 | 1/2009 | Dala-Krishna | |
| 2009/0018526 A1 | 1/2009 | Power et al. | |
| 2009/0036780 A1 | 2/2009 | Abraham | |
| 2009/0132019 A1 | 5/2009 | Duffy et al. | |
| 2009/0171293 A1 | 7/2009 | Yang et al. | |
| 2009/0177035 A1 | 7/2009 | Chin | |
| 2009/0240253 A1 | 9/2009 | Murray | |
| 2009/0254116 A1 | 10/2009 | Rosenschein et al. | |
| 2009/0270975 A1 | 10/2009 | Giofford, III et al. | |
| 2009/0319017 A1 | 12/2009 | Berez et al. | |
| 2010/0016943 A1 | 1/2010 | Chobotov | |
| 2010/0024818 A1 | 2/2010 | Stenzler et al. | |
| 2010/0030165 A1 | 2/2010 | Takagi et al. | |
| 2010/0030256 A1 | 2/2010 | Dubrul et al. | |
| 2010/0069852 A1 | 3/2010 | Kelley | |
| 2010/0168583 A1 | 7/2010 | Dausch et al. | |
| 2010/0185161 A1 | 7/2010 | Pellegrino et al. | |
| 2010/0185231 A1 | 7/2010 | Lashinski | |
| 2010/0204708 A1 | 8/2010 | Sharma | |
| 2010/0268067 A1 | 10/2010 | Razzaque et al. | |
| 2010/0272740 A1 | 10/2010 | Vertegel et al. | |
| 2010/0298922 A1 | 11/2010 | Thornton et al. | |
| 2011/0009943 A1 | 1/2011 | Paul et al. | |

(56) References Cited

U.S. PATENT DOCUMENTS

| | | |
|---|---|---|
| 2011/0034987 A1 | 2/2011 | Kennedy |
| 2011/0071394 A1 | 3/2011 | Fedinec |
| 2011/0082533 A1 | 4/2011 | Vardi et al. |
| 2011/0224773 A1 | 9/2011 | Gifford et al. |
| 2011/0230830 A1 | 9/2011 | Gifford, III et al. |
| 2011/0270375 A1 | 11/2011 | Hartley et al. |
| 2012/0016343 A1 | 1/2012 | Gill |
| 2012/0020942 A1 | 1/2012 | Hall et al. |
| 2012/0022636 A1 | 1/2012 | Chobotov |
| 2012/0029478 A1 | 2/2012 | Kurosawa |
| 2012/0034205 A1 | 2/2012 | Alkon |
| 2012/0035590 A1 | 2/2012 | Whiting et al. |
| 2012/0169712 A1 | 7/2012 | Hill et al. |
| 2012/0209375 A1 | 8/2012 | Madrid et al. |
| 2012/0289945 A1 | 11/2012 | Segermark |
| 2013/0053792 A1 | 2/2013 | Fischell et al. |
| 2013/0131777 A1 | 5/2013 | Hartley et al. |
| 2013/0296773 A1 | 11/2013 | Feng et al. |
| 2013/0331819 A1 | 12/2013 | Rosenman et al. |
| 2013/0331921 A1 | 12/2013 | Roubin |
| 2014/0031925 A1 | 1/2014 | Garrison et al. |
| 2014/0142427 A1 | 5/2014 | Petroff |
| 2014/0214002 A1 | 7/2014 | Thermopeutix |
| 2014/0228808 A1 | 8/2014 | Webster et al. |
| 2014/0358123 A1 | 12/2014 | Ueda et al. |
| 2015/0018942 A1 | 1/2015 | Hung et al. |
| 2015/0174377 A1 | 6/2015 | Syed |
| 2015/0190576 A1 | 7/2015 | Lee et al. |
| 2015/0201900 A1 | 7/2015 | Syed |
| 2015/0245933 A1 | 9/2015 | Syed |
| 2015/0352331 A1 | 12/2015 | Helm, Jr. |
| 2015/0366536 A1 | 12/2015 | Courtney et al. |
| 2015/0374261 A1 | 12/2015 | Grunwald |
| 2016/0008058 A1 | 1/2016 | Hu et al. |
| 2016/0038724 A1 | 2/2016 | Madsen et al. |
| 2016/0120509 A1 | 5/2016 | Syed |
| 2016/0120673 A1 | 5/2016 | Siegel et al. |
| 2016/0296355 A1 | 10/2016 | Syed |
| 2016/0338835 A1 | 11/2016 | Bioventrix |
| 2017/0119562 A1 | 5/2017 | Syed |
| 2017/0135833 A1 | 5/2017 | Syed |
| 2017/0181876 A1 | 6/2017 | Syed |
| 2017/0304095 A1 | 10/2017 | Syed |
| 2017/0361062 A1 | 12/2017 | Syed |
| 2018/0042743 A1 | 2/2018 | Syed |
| 2018/0059124 A1 | 3/2018 | Syed |
| 2018/0116780 A1 | 5/2018 | Laine |
| 2018/0250147 A1 | 9/2018 | Syed |
| 2019/0091441 A1 | 3/2019 | Syed |

FOREIGN PATENT DOCUMENTS

| | | |
|---|---|---|
| CN | 108882975 A | 11/2018 |
| CN | 109475722 A1 | 3/2019 |
| EP | 3280355 A1 | 2/2018 |
| EP | 3367969 A1 | 9/2018 |
| EP | 3368123 A1 | 9/2018 |
| EP | 3399944 A1 | 11/2018 |
| EP | 3405261 A1 | 11/2018 |
| IN | 201827018555 A | 10/2018 |
| IN | 201827018768 A | 10/2018 |
| WO | 1996036269 | 11/1996 |
| WO | 2011/011539 A1 | 1/2011 |
| WO | WO2011/106502 | 9/2011 |
| WO | 2010/129193 A1 | 11/2011 |
| WO | 2011/137336 A1 | 11/2011 |
| WO | 2012030101 | 8/2012 |
| WO | 2014081947 | 5/2014 |
| WO | 2014197839 | 12/2014 |
| WO | 2016164215 | 10/2016 |
| WO | 2017/074492 A1 | 5/2017 |
| WO | 2017/074536 A1 | 5/2017 |
| WO | 2017/127127 A1 | 7/2017 |
| WO | 2017222571 A1 | 12/2017 |
| WO | 2017222612 A1 | 12/2017 |
| WO | 2018/164766 A1 | 9/2018 |
| WO | 2019/070349 A1 | 4/2019 |

OTHER PUBLICATIONS

International Preliminary Report on Patentability issued in International Application No. PCT/US2013/071271 dated May 26, 2015, 6 pages.
Office Action issued in U.S. Appl. No. 13/750,920 dated Apr. 8, 2015.
Response to Office Action in U.S. Appl. No. 13/750,920 dated Aug. 10, 2015.
Supplemental Response to Office Action in U.S. Appl. No. 13/750,920 dated Nov. 2, 2015.
Office Action in U.S. Appl. No. 13/750,920 dated Nov. 5, 2015.
Response to Office Action in U.S. Appl. No. 13/750,920 dated Feb. 11, 2016.
International Search Report / Written Opinion issued in Int'l Application No. PCT/US2016/024794 dated Jul. 1, 2016, 10 pages.
International Search Report and Written Opinion issued for PCT/US2018/012834 dated Mar. 15, 2018, 13 pages.
Godwin, J., The Circulatory and Respiratory Systems, Z0250 Lab III, 2002, retrieved from: https://projects.ncsu.edu/cals/course/zo250/lab-3.html.
Stroke Treatments, American Heart Association, Retrieved from: Http://www.strokeassociation.org/STROKEORG/AboutStroke/Treatment/Stroke-Treatments_UCM_310892_Article.jsp#V9Hrg2WfV_1.
Beckman et al., Venous Thromboembolism: A Public Health Concern, Am J Prev Med., 2010, vol. 38(4), pp. S495-S501.
Meunier et al., Individual Lytic Efficacy of Recombinant Tissue Plasminogen Activator in an in-vitro Human Clot Model: Rate of Nonresponse Acad Emerg Med., 2013, vol. 20(5), pp. 449-455.
Tripathi et al., Use of Tissue Plasminogen Activator for Rapoid Dissolution of Fibrin and Blood Clots in the Eye After Surgery for Claucomoa and Cataract in Humans, Drug Development Research, 1992, vol. 27(2), pp. 147-159.
International Search Report and Written Opinion for International Application No. PCT/US2016/024795 dated Aug. 30, 2016, 14 pages.
International Search Report and Written Opinion issued for International Application No. PCT/US2016/047165 dated Jan. 5, 2017, 13 pages.
International Preliminary Report on Patentability issued in International Application No. PCT/US2016/024795 dated May 1, 2018, 10 pages.
International Preliminary Report on Patentability issued in International Application No. PCT/US2016/047165 dated May 1, 2018, 5 pages.
International Search Report and Written Opinion issued for International Application No. PCT/US2017/021188 dated May 10, 2017, 11 pages.
Schwartz et al., Intracardiac Echocardiography in Humans using a Small-Sized (6F), Low Frequency (12.5 MHz) Ultrasound Catheter Methods, Imaging Planes and Clinical Experience, Journal of the American College of Cardiology, 1993, vol. 21(1), pp. 189-198.
Blaney et al., Alteplase for the Treatment of Central Venous Catheter Occlusion in Children: Results of a Prospective, Open-Label, Single-Arm Study (The Cathflo Activase Pediatric Study).
International Preliminary Report on Patentability issued for PCT/US2017/021188 dated Dec. 25, 2018, 9 pages.
International Preliminary Report on Patentability issued for PCT/US2016/047163 dated Dec. 25, 2018, 7 pages.
International Search Report and Written Opinion for PCT/US2018/047372 dated Jan. 2, 2019, 8 pages.
EP 16777055.1 Extended Search Report dated Feb. 12, 2019, 7 pages.
International Search Report and Written Opinion for International Application No. PCT/US2019/012727 dated Mar. 21, 2019, 12 pages.

(56) References Cited

OTHER PUBLICATIONS

International Search Report and Written Opinion for International Application No. PCT/US2019/12745 dated Apr. 1, 2019, 10 pages.
Shah, T., Radiopaque Polymer Formulations for Medical Devices, MDDI Medical Diagnostic and Device Industry: Materials, 2001, retrieved from: https://www.mddionline.com/radiopaque-polymer-formulations-medical-devices.

* cited by examiner

Cross section of the bifurcated catheter within the sheath catheter close to the point of bifurcation ( Not to scale)

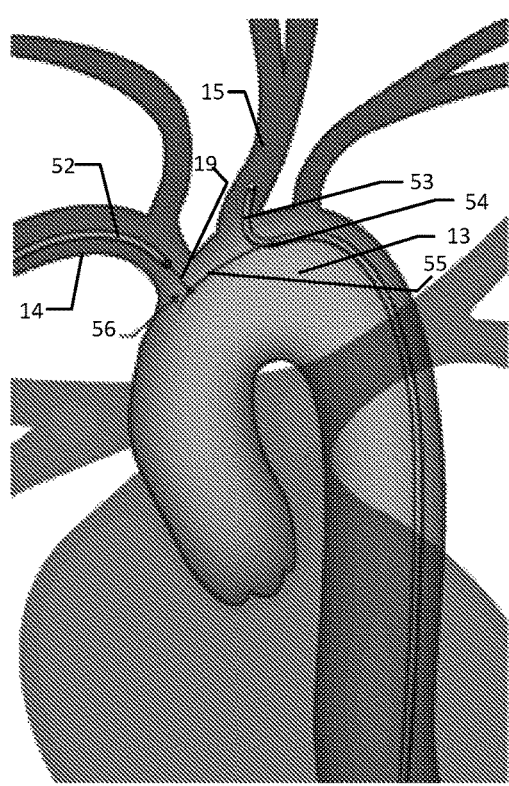 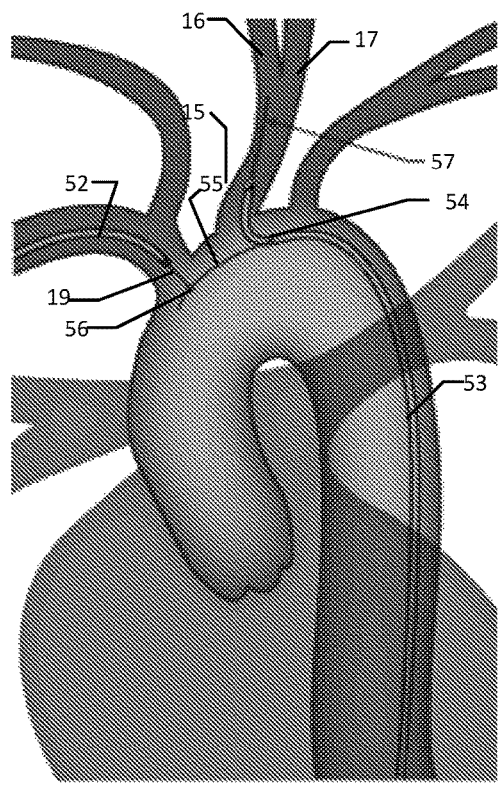
Figure 11                    Figure 12

APPARATUS AND METHOD FOR STABILIZATION OF PROCEDURAL CATHETER IN TORTUOUS VESSELS

CROSS-REFERENCE TO RELATED APPLICATIONS

The present application is a continuation-in-part application of U.S. patent application Ser. No. 14/929,030 entitled "Apparatus and Method for a Bifurcated Catheter for Use in Hostile Aortic Arches", filed Oct. 30, 2015, now U.S. Pat. No. 9,980,030, the entirety of which is herein incorporated by reference.

The present patent application also claims priority to provisional application No. 62/352,353, entitled "Apparatus and Method for Stabilization of Procedural Catheter in Tortuous Vessels", filed Jun. 20, 2016, the entirety of which is herein incorporated by reference.

BACKGROUND

1. Field

The invention relates to improved methods and apparatus used in catheter based interventional procedures, mainly involving hostile vessels, and access for semi-invasive procedures, such as stenting.

2. Related Art

Stenting of the carotid artery (CA) is relatively new to interventional procedures. It is a challenging procedure because accessing the left or right carotid artery can be dependent on the anatomical disposition of the aortic arch.

FIG. 1 illustrates the aortic arch. As shown in FIG. 1, the aorta 1 includes an aortic arch region 3, a descending aorta 2, and an innominate 4. Three types of arches shown in FIG. 1: Type I, Type II and Type III arches. Also shown in FIG. 1 is the right subclavian artery (RSA) 5, left subclavian artery (LSA) 6, right common carotid artery (RCCA) 7 and left common carotid artery (LCCA) 8.

The arch types are defined by the height of the top of the aortic arch 3 from the base location where the innominate 4 attaches to the aorta. In a type I arch, the height is less than the diameter of the common carotid artery (CCA). Similarly, in a type II arch, the height of the top of the arch 3 from the base of the innominate 4 is of the order of 1 to 2 times the diameter of the CCA. In a type III arch, the height is more than twice the diameter of the CCA. As the height of the arch increases the procedures within the carotid arteries become more and more difficult due to the tortuous nature of the arterial connections to the aorta at the arch.

In type III hostile aortic arches, the angle of origin of the innominate artery or left common carotid artery can be very acute thus making the access of the left or right carotid arteries ostium difficult. Subsequent placement of a stent delivery system in a stable mode into the arterial system above it therefore becomes more difficult. The stenting procedure itself is meant to re-establish a more normalized blood flow through the carotid and internal carotid artery into the brain by opening up regions of the artery constricted by plaque deposits which inhibit flow. The stents themselves can be self-expanding, balloon expandable, bio-absorbable, and/or covered. The stent delivery systems are designed to accommodate very acute bends but are reliant upon the guide catheter and guide wires and or embolic protection devices to stabilize them during deployment. Stents have been used to open "stenosis"—semi-occluded sections of the arterial system—for many years. They come in a wide variety and are designed for specific areas of the body, these include: balloon expandable, self-expanding, covered and bio-absorbable stents. Stenting in the neck and procedures above the neck are challenging when confronted with a type III hostile aorta, in particular stenting of the left or right carotid artery. During the insertion, manipulation and stabilization of the stent delivery mechanism and during removal of the guide wire and secondary wire, injuries to the subclavian artery and the tortuous aortic arch can happen. This can be caused by uncontrolled collapse of the sheath, embolic protection device (EPD) and stent/stent delivery system in the ascending aorta during procedure. This type of prolapse can result in the patient suffering cerebral embolism or stroke by dragging the fully deployed EPD over the carotid stenosis. Further, dragging the guide wires over the tortuous arterial regions can cause cutting into the arterial walls or otherwise injuring the artery resulting in dissections and trauma to the vessels involved. These traumas can be dangerous to the patient as they can ultimately directly affect blood flow by leakage at the dissections or by creating accumulation of thrombus, an organization of blood cells, which is a natural reaction to vessel injury. These may require additional procedures to repair and heal the damaged artery walls and prevent problems.

Accordingly, what is needed is systems and methods to stabilize the sheath, the EPD and the stent delivery system within the carotid arterial system to reduce the injuries caused to the arterial walls during stenting and other minimally invasive treatment of the carotid arteries and above the neck procedures.

SUMMARY

The following summary of the invention is included in order to provide a basic understanding of some aspects and features of the invention. This summary is not an extensive overview of the invention and as such it is not intended to particularly identify key or critical elements of the invention or to delineate the scope of the invention. Its sole purpose is to present some concepts of the invention in a simplified form as a prelude to the more detailed description that is presented below.

In accordance with one aspect of the invention, systems and methods are disclosed for the use of a twin catheters in single sheath (snare catheter/snared wire and procedural sheath)—one for the stabilization wire and the other for the procedure.

In accordance with another aspect of the invention, systems and methods are disclosed for the implementation of the twin catheters/sheaths or a catheter and stabilization wire without the bifurcated catheter with a Tuohy Borst adapter to prevent blood leakage.

In accordance with another aspect of the invention, systems and methods are disclosed for the use of the single sheath to stabilize the procedural catheter for use in procedures in adverse tortuous anatomy for minimally invasive procedures through both venous or arterial access.

In accordance with another aspect of the invention, systems and methods are disclosed for the use of the bifurcated sheath and the dual sheath for in treatment of contralateral lower extremity peripheral arterial disease with a complex or hostile aortic bifurcation (due to a fixed and narrow aortic bifurcation, iliac stenosis, ectasia, or tortuosity, aneurysm of the distal aorta, previous iliac stenting, previous endovascular aneurym repair and previous aortofemoral/aortoiliac bypass grafting etc.) using bilateral groin access, renal and other visceral interventions such as renal and SMA, stenting and cancer hepatic embolizations, and splenic arterial interventions (using groin and radial artery access).

In accordance with another aspect of the invention, systems and methods are disclosed for the use of the bifurcated side hole catheter or the 'Y' catheter for providing stabilization to the procedural catheter during procedures where tortuous branching of vessels make stability important, such as:

1. Use in complex or hostile aortic bifurcation application.
2. Use in Visceral Interventions.

BRIEF DESCRIPTION OF THE DRAWINGS

The accompanying drawings, which are incorporated into and constitute a part of this specification, illustrate one or more examples of embodiments and, together with the description of example embodiments, serve to explain the principles and implementations of the embodiments.

FIG. 6A is a cross-sectional view of a portion of the bifurcated catheter in accordance with one embodiment of the invention.

FIG. 11 is a schematic diagram illustrating capturing the stabilization wire by the snare wire loop in accordance with one embodiment of the invention.

FIG. 12 is a schematic diagram of the extension of a stiff guide wire from the reverse curve Simmons catheter into the carotid artery in accordance with one embodiment of the invention.

DETAILED DESCRIPTION

Figure 1:
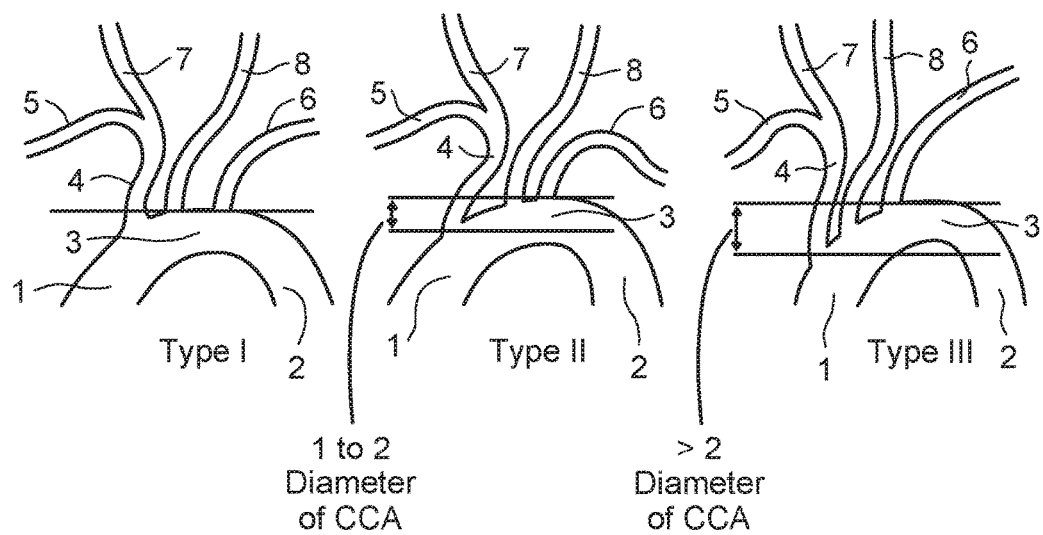
FIG. 1 is a schematic diagram illustrate the three types of aortic arches encountered in humans.

Embodiments of the invention are directed to new devices and associated methods for the placement of stents in the carotid artery, and especially into the left or right carotid arteries, for procedures above the neck. These new devices and associated methods stabilize the working lumen or delivery sheath for the carotid stent delivery system. These new devices and associated methods also protect the innominate and subclavian artery as well as the aortic arch from trauma during stenting and other procedures above the neck where there is a possibility for trauma to the arteries as a result of tension on the secondary or stabilization guidewire. This is especially true in the case of patients with type II and Type III aortic arch.

Embodiments of the invention are directed to the application and use of guide wires for stabilization of the catheters used to access the left or right carotid arteries (CA) for carotid percutaneous intervention of the vessels originating from a tortuous aortic arch.

Embodiments of the invention use a bifurcated catheter having a main catheter arm that is used to extend into the region of the procedure and a support catheter arm that extends into the right subclavian artery to provide protection to that vessel during tightening of a support and stabilization wire through the right subclavian artery. The head of a sheath/guide catheter is at that time placed in the aorta, at the branching of either innominate or the left or right carotid artery through which the procedural arm of the bifurcated catheter, that is the second branch of the bifurcated catheter, has to be extended to conduct the procedure or place the stent. The correct placement of the head of the sheath catheter and the extension of the support catheter to cover the support wire enable the wires to be extended and retracted without damage to the arch and the arterial vessels used during procedure.

In some embodiments, the bifurcated catheter includes a main catheter that divides into two separate catheters forming a "Y" shape. One leg of the bifurcated catheter has a smaller diameter with a smaller working lumen (inner diameter) to carry the stabilizing wire and the second leg of the bifurcated catheter has a larger working lumen for arterial stenting operations/procedures. This bifurcated catheter addresses the percutaneous intervention related trauma to the vessels that arise from type-II or type-III hostile aortic arches, from uncontrolled prolapse of the sheath, embolic protection device and stent delivery system, by stabilizing the systems, using a through-and-through stabilization wire for applying tension during stenting of the left and right carotid arteries.

Similar to type III aortic arches, tortuosity due to a bovine arch (origin of left common carotid artery from the innominately artery rather than directly from the aotic arch), tortuousity of the common carotid artery and even internal carotid artery (including angulated takeoff of the internal carotid artery) may be quite amenable to the disclosed unique sheath system. In addition, standard technique depends on placing a stiff wire in the external carotid artery for support to advance the sheath into the distal common carotid artery. The sheath described herein circumvents the need for an external carotid artery access which is otherwise crucial for the standard technique. Also, the device, due to its unique stability, may also allow larger caliber proximal protection devices (which depend on reversal of internal carotid flow during stenting to prevent cerebral embolization) to be deployed more easily. Similarly, the bifurcated catheter is useful in complex or hostile aortic bifurcation application and visceral interventions.

In one embodiment, a sheath catheter is percutaneously inserted at the groin and directed through the descending aorta to the aortic arch. A snare is inserted through the sheath and linked with a 0.014 inch or 0.018 inch guide wire from the right subclavian artery (via the right radial or brachial artery access) to provide a stabilization wire for the operational catheter. At this stage, the stabilization wire and the main guide wire occupy the sheath catheter. A reverse curve catheter is then inserted through the sheath catheter over the main guide wire, parallel to the stabilization wire and guided to the common carotid artery from the aortic arch. A stiff guide wire is then inserted through the reverse catheter to the location of the procedure. The reverse curve catheter is then removed leaving the guide wire in the location of the procedure. The bifurcated catheter is then guided to the aortic arch with one stabilization leg over the stabilization wire and the other operational leg over the stiff guide wire such that the operational leg is guided into the common carotid artery while the stabilization leg is guided over the stabilization wire into the subclavian artery. The stiff guide wire is then removed leaving the operational leg of the bifurcated catheter in place for treatment procedures.

In one embodiment, a secondary stabilization wire having a small diameter, e.g., 0.014 or 0.016 inch, is guided through a, for example, Fr-3 or Fr-5, micro sheath, which is placed percutaneously through the right radial or brachial artery and threaded through the subclavian artery and snared into the main guide catheter to stabilize the distal tip. This way, the tension can be applied to the distal tip of the guide catheter to stabilize it in a more planar orientation by putting tension on the stabilization wire, as discussed above, to aid in the stabilization of the guide catheter, which is placed under fluoroscopy (C Arm) in the aorta using percutaneous access. This secondary stabilization wire is hence inserted into the right radial or brachial artery and guided through the right subclavian artery and down and out of the guide catheter. Though the description is provided for the secondary access via the right radial of brachial artery, it should not be considered limiting. It is possible to provide the secondary access via the left radial or brachial artery, external carotid artery or common carotid artery (instead of just the right radial or brachial artery). It may also be possible to have more than one accessory access to complete the procedure using the device. Once the stabilization wire is established, a tension is applied to one or both ends of the secondary stabilization wire to help stabilize the distal end of the guide catheter during the accessing of the left or right internal carotid artery. This allows the stent delivery system to track more easily through the acute anatomy of the arch, especially one such as a type III arch.

In another embodiment, the bifurcated catheter is pre-loaded into the end of the main guide catheter or long sheath. In this embodiment, the bifurcated catheter has a procedural lumen and a second lumen that can accommodate a snare catheter and wire. It will be appreciated, however, that a potential disadvantage of this device is that the catheter will need to be a bigger device to accommodate the two lumens, but the advantage is that it separates the wires from the beginning so that the wires do not inadvertently wrap around each other during the procedure and cause problems. In this embodiment, the guide catheter is provided with a bifurcated distal configuration having two legs in the form of a Y at the distal end. One leg is of a large diameter, typically having an inner diameter or "working lumen" sufficient to allow the passage of a stent delivery system or other therapeutic devices. The second leg is of a smaller diameter than the first leg with an inner diameter sufficient to accept a snare wire and snare the stabilization guide wire. This bifurcated catheter is sized so as to fit easily through the main guide catheter placed at the start of the procedure and is of sufficient length so as to allow the main leg of the bifurcated catheter to be placed into the carotid artery for stenting and other procedures there and above the neck. The secondary leg is of sufficient length so as to be placed over a stabilization wire from the right subclavian artery and cover it sufficiently to prevent damage to the vessels it passes through while providing the necessary stabilization to the main guide catheter and the bifurcated catheter, during procedural manipulations. Both legs of the bifurcated catheter need not be of the same stiffness or durometer to be able to navigate their respective vessels. For instances the main carotid leg may be of a lesser durometer so as to navigate the arch into the selected carotid artery without affecting the natural anatomic configuration whereas the small leg may be stiffer so as to help with the stabilization of the main guide catheter.

In one embodiment, another practical device and method for safely accessing the carotid artery is disclosed. In this a first reverse curve catheter is inserted percutaneously and directed into the right or left common carotid artery (RCCA or LCCA). A secondary wire is inserted in the reverse curve catheter and out of a hole in the catheter at the location of the arch to be captured by a snare wire that is extended out of a protective sheath extended through the subclavian artery (typically via right radial artery access). Once the snare has captured the stabilization wire a more rigid guide wire is extended through the reverse catheter into the common carotid artery towards the location of the procedure. The reverse catheter is then removed leaving both the rigid guide wire and the stabilization wire in place. A sheath/procedural catheter with a conical atraumatic tip and also having therein a second chamber with a hole close to the distal end for providing an exit for the stabilization wire is advanced over the guide wire and stabilization wires to the aortic arch and the sheath catheter is extended on to the location of procedure. Tension is applied to the stabilization wire for providing support to any working catheter that is inserted through the sheath catheter after removal of the stiff guide wire for conducting the procedure as needed.

In some embodiments, a sheath cover may be used for the stabilization wire as it extends into the subclavian artery when tension is applied prevent unwanted damage to the artery. The stabilized main sheath helps the procedure to be completed and the operational catheter and the sheath catheter to be removed safely.

In some embodiments, a reverse curve guide catheter with a lumen large enough for stenting is used to select the common carotid artery. A secondary wire is inserted in the reverse curve catheter through a parallel lumen in the reverse curve catheter and out of a hole in the catheter at the location of the arch. This secondary wire is then captured by a snare wire with a loop that is extended out of a protective sheath extended through the subclavian artery, typically inserted via right radial artery access. The carotid stenting procedure can now proceed in the standard way described above since the reverse curve guiding catheter itself is stabilized and is usable for procedure.

Further to the above, the bifurcated catheter is ideal for providing stabilization to the procedural catheters used in treatment of contralateral lower extremity peripheral arterial disease with a complex or hostile aortic bifurcation (due to a fixed and narrow aortic bifurcation, iliac stenosis, ectasia, or tortuosity, aneurysm of the distal aorta, previous iliac stenting, previous endovascular aneurym repair and previous aortofemoral/aortoiliac bypass grafting) using bilateral groin access.

In percutaneous procedures of the vessels originating from a tortuous aortic arch, the use of stabilization wires in addition to guide wires to guide and stabilize the delivery catheters used to access the left or right carotid arteries is disclosed. The need for the stabilization of the sheath, the embolic protection device (EPD) and the stent delivery system (SDS) is to prevent the uncontrolled prolapse of the sheath, EPD and SDD during stenting procedure in the ascending aorta. This type of prolapse can result in cerebral embolism or stroke in patients by the dragging of the fully deployed EPD across critical carotid internal artery stenosis. Embodiments of the invention provide for stabilizing the sheath, the EPD and the SDS within the left or right carotid arteries by providing a secondary stabilization wire that holds the primary sheath in place within the tortuous aortic arch during the procedure, thereby providing the necessary stability for the SDS within the carotid artery during the procedure. These stabilizing wires typically originate from a low profile radial or brachial artery access and provide a through-and-through tension and support to the sheath by enabling the application of tension to one or either end of the stabilization wire through a typical micro-sheath or catheter. In this embodiment the brachial artery or a small radial artery is usable with the micro-sheath, and similarly in the case of another embodiment described the sheath catheter is used to puncture the radial artery or the brachial artery for entry, to provide adequate hemostasis while keeping the entry profile low. In one embodiment, the stabilization wire has a small diameter, e.g., 0.014 or 0.018 inch diameter, the micro-sheath has a 3 Fr. Diameter, and the sheath catheter has a 5 Fr. Diameter. The use of the small size wire and micro-sheath is useful in preventing hematoma in the brachial artery, which can be devastating in patients receiving anticoagulation drugs, such as Heparin, and anti-platelet therapy such as Plavix, during or after the procedure. The stabilizing wire from the brachial artery enters the aortic arch through the right subclavian artery to be captured and brought out through the sheath at its proximal end. Due to their diameter and forces applied during the procedures, the guide wires, if used without proper covering can inadvertently cause trauma to the associated tortuous vessels walls. The bifurcated catheter disclosed herein provides the necessary protection to the arch and the subclavian artery while providing the necessary stabilization to the sheath, SDS and EPD for access and procedures within the carotid arteries, especially for above the neck procedures. The bifurcated catheter disclosed includes a main catheter that divides into two separate catheters forming a "Y" shape. One leg of the catheter has a smaller diameter with a smaller working lumen (inner diameter), to carry the stabilizing wire, than the second leg of the catheter that has a larger working lumen for arterial stenting operations. This device provides the necessary stability to the system for stenting of the carotid arteries while addressing the percutaneous intervention related trauma to the vessels associated with type-III hostile aortic arches that arise therefrom. Multiple embodiments of the invention are described here under. Even though in the examples described the secondary access is shown as being established via the right radial or brachial artery, it should not be considered limiting in any way. The secondary access may be established via any of the left radial or brachial artery, external carotid artery or common carotid artery (instead of just the right radial or brachial artery). It may also be possible to have more than one accessory access to complete the procedure using the device.

A first embodiment of the invention is described with reference to the schematic diagrams shown in FIGS. 2 to 7 and the flow chart of FIG. 8A. This embodiment illustrates the ability to conduct procedures such as stenting in the left internal carotid artery (LICA) 16 using a procedural catheter that can be inserted through the aortic arch 13 and left common carotid artery 15.

Figure 2:
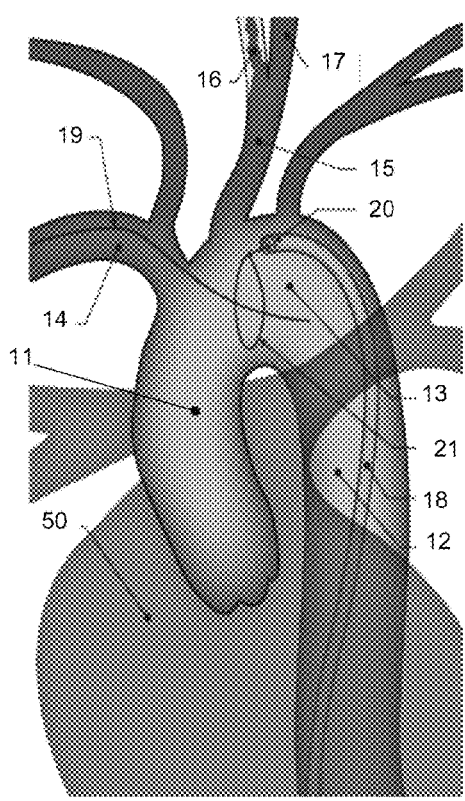
FIG. 2 is a schematic diagram illustrating a distal end of a device with a snare wire extended from the main guide catheter capturing a stabilization wire from the subclavian artery (SA) in accordance with one embodiment of the invention.

As shown in FIG. 2, a sheath catheter 18 is initially inserted percutaneously and guided using fluoroscopic tracking using the opaque metal ring 20 at its distal end. In one embodiment, the sheath catheter 18 is a 7 French (Fr) or 8 Fr sheath; it will be appreciated that differently sized sheath catheters may be used as known to those of skill in the art. The sheath 18 is guided through the femoral artery and the descending thoracic aorta 12 to the aortic arch 13. A snare wire is inserted through the sheath 18 and extended to the aortic arch 13 with a snare loop 21. In one embodiment, the snare loop has a diameter that is any value or range of values between about 20 to 30 mm; it will be appreciated that the diameter may be less than about 20 mm or greater than about 30 mm.

Figure 3:
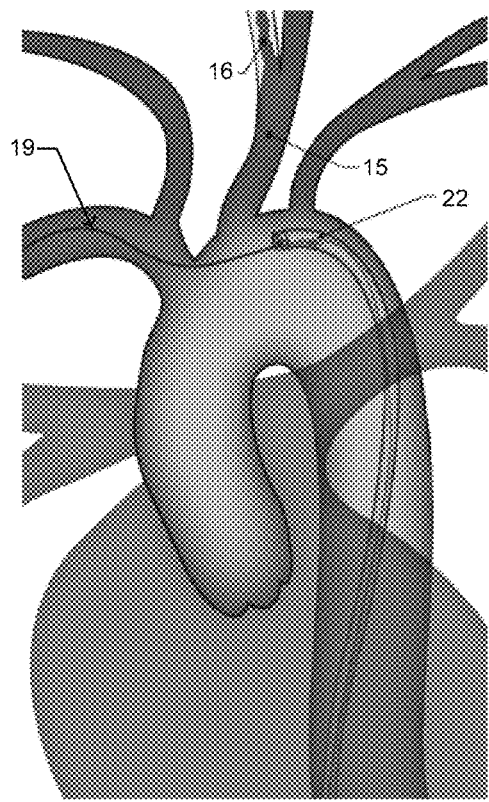
FIG. 3 is a schematic diagram illustrating the aortic arch with a stabilization guide wire snared and pulled into the main guide catheter and out the proximal end in accordance with one embodiment of the invention. The bifurcated catheter may or may not be at this stage located just inside the distal tip of the main guide catheter. The bifurcated catheter in one embodiment may be advanced over the wire after step S808A (FIG. 8A) while in another embodiment the bifurcated catheter may be pre-loaded at the distal tip of the main guide catheter (FIG. 8B).

A second stabilization wire 19 is inserted through the radial artery and guided through the subclavian artery 14 to the aortic arch 13. In one embodiment, the second stabilization wire has about a 0.014 inch diameter. The stabilization wire 19 is captured by the snare 21 and then pulled into the sheath catheter 18, as shown in FIG. 3. In one embodiment, the snare 21 pulls the stabilization wire such that it exits the proximal end of the sheath 18 to form a through-and-through stabilization wire. In one embodiment, a 3 Fr. to 5 Fr. sheath may be used over the 0.014 stabilization wire 19 to reduce slicing and trauma to the arteries the wire is guided through.

Figure 4:
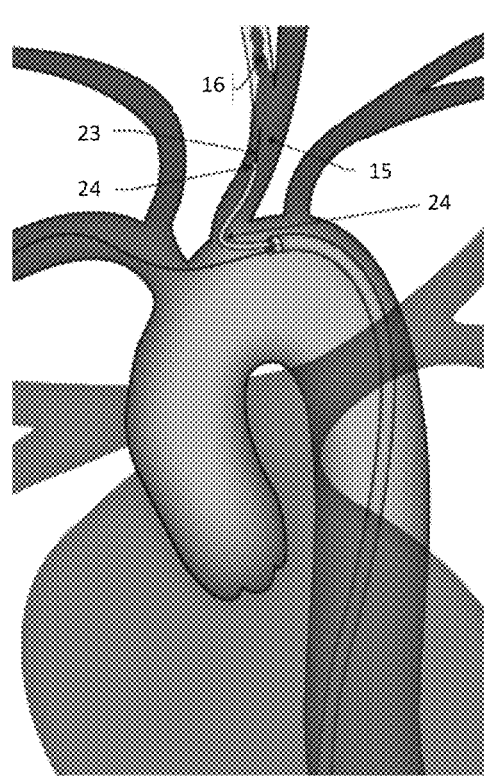
FIG. 4 is a schematic diagram illustrating a reverse curve diagnostic catheter with a guide wire coming out of in the distal tip of the main guide catheter and up into the left common carotid artery in accordance with one embodiment of the invention. In one embodiment, the reverse curve diagnostic catheter with the guide wire is extended out of the sheath or the main guide catheter, and in another embodiment, the bifurcated catheter is at the distal tip of the main guide catheter and the reverse curve diagnostic catheter with the guide wire comes out of the larger leg of the bifurcated catheter.

A reverse curve catheter 24 with an atraumatic tip is then inserted in parallel with the stabilization wire 19 through the sheath catheter 18, as shown in FIG. 4. The reverse curve catheter 24 is used to select the left common carotid artery 15. A stiff wire 23 is then inserted through the reverse curve catheter 24 to the site of the procedure. In one embodiment, the stiff wire has an approximately 0.035 inch diameter.

Figure 5:
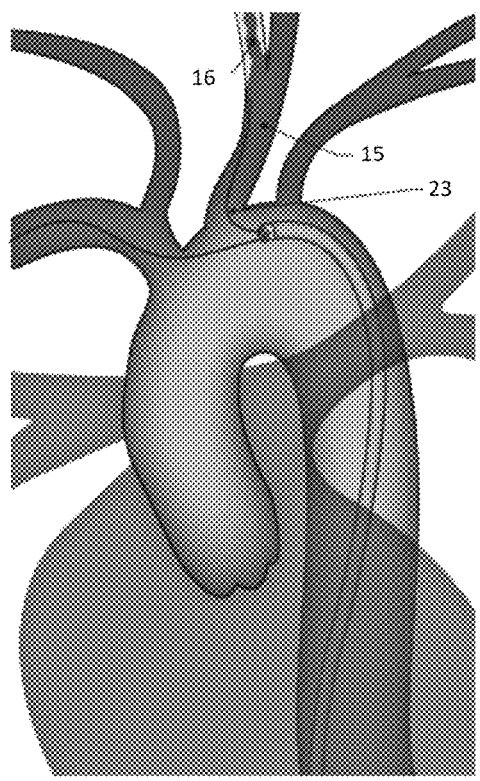
FIG. 5 is a schematic diagram illustrating removal of a reverse curve diagnostic catheter, leaving behind a stiff guide wire in the left common carotid artery in accordance with one embodiment of the invention.

Next, the reverse curve catheter 24 is removed, leaving the stiff wire 23 in the area of the procedure and the stabilization wire 19 in place, as shown in FIG. 5. Both the stiff wire 23 and stabilization wire 19 occupy the large sheath catheter 18, as shown in FIG. 5.

Figure 6:
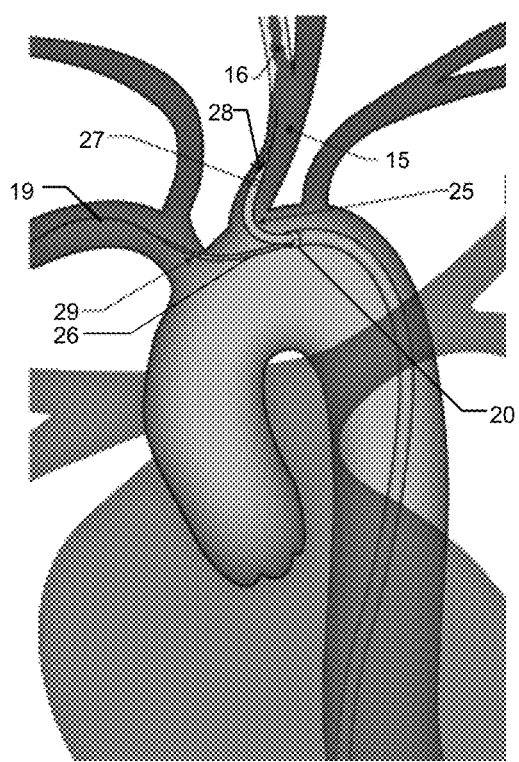
FIG. 6 is a schematic diagram illustrating a bifurcated catheter being advanced out of a main guide catheter over respective guide wires, the large leg over the stiff guide wire into the left common carotid artery and the small leg being advanced over the guide wire into the right subclavian artery in accordance with one embodiment of the invention.

A bifurcated catheter having bifurcations 25 and 26 is then advanced over both the stiff wire 23 and the stabilization wire 19 respectively and out of the guide catheter 18. The large leg (or bifurcation) 25 which contains a procedural catheter tracks along the stiff guide wire 23 into the left common carotid artery 15. The small leg (or bifurcation) 26 tracks along the stabilization wire 19 coming from the right subclavian/innominate artery. Both legs 25, 26 have atraumatic tips 28 to reduce trauma, as shown in FIG. 6.

FIG. 6A is a cross-sectional view of a portion of the bifurcation catheter within the sheath catheter 18. The bifurcation catheter includes a common catheter portion that bifurcates into two separate bifurcations or legs 25, 26 at junction 30. As shown in FIG. 6A, each of the bifurcations of legs 25, 26 include lumens that extend from a distal end of the bifurcation catheter to a proximal end of the bifurcation catheter. As shown in FIG. 6A, the bifurcated leg 25 is configured to slideably receive the guidewire 23, and the bifurcated leg 26 is configured to slideably receive the stabilization wire 19.

Figure 7:
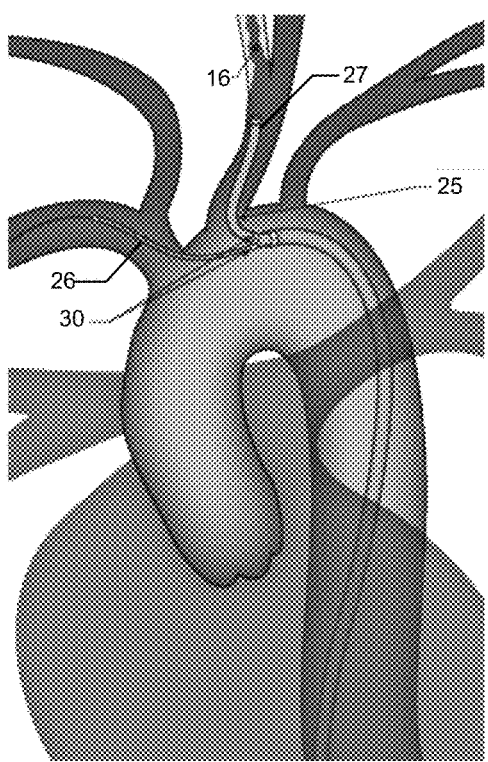
FIG. 7 is a schematic diagram of the legs of the bifurcated catheter advanced out of the main guide catheter and parked into their respective vessels in accordance with one embodiment of the invention. In some embodiments, the atraumatic tips are removed from each leg and the stabilized catheter is ready for procedures.
Figure 6:
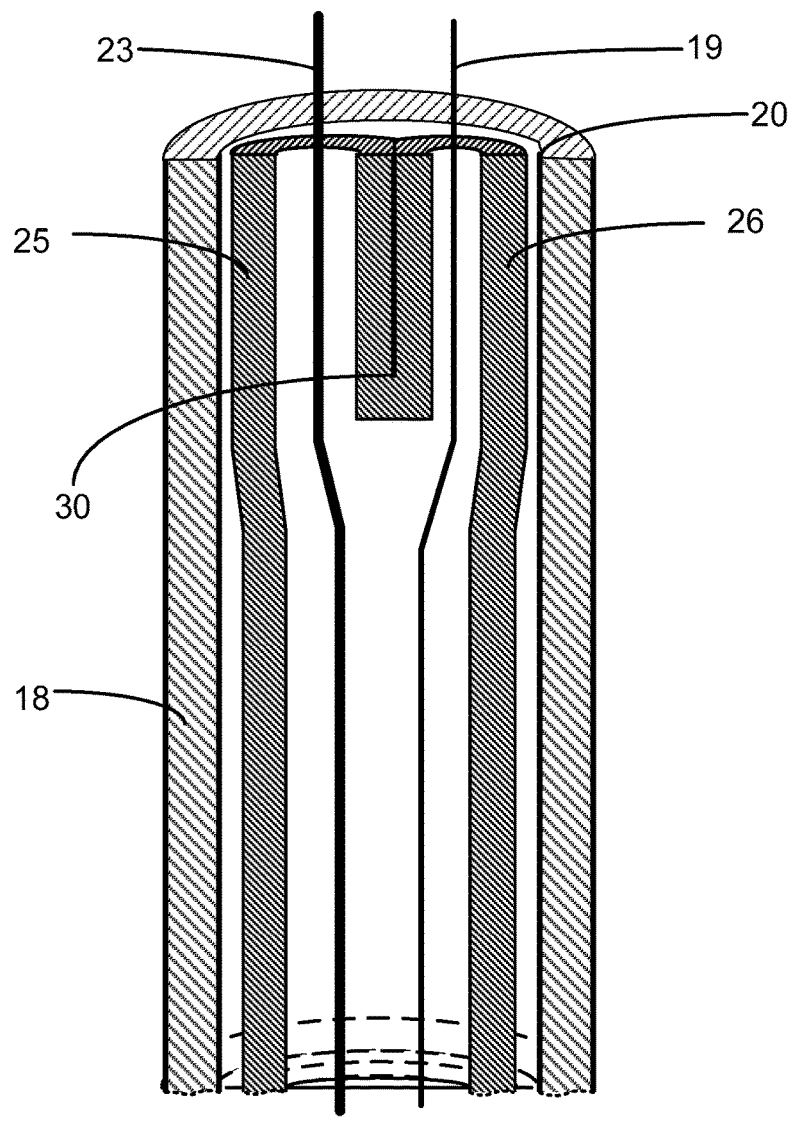

Once the bifurcated catheter is in place, the stiff wire and the atraumatic tips are removed and tension is applied to the stabilization wire from both ends to stabilize and position the operational end of the bifurcated catheter, as shown in FIG. 7.

The bifurcated catheter is now ready for stenting or other procedures in the left internal carotid artery 16.

Figure 8A:
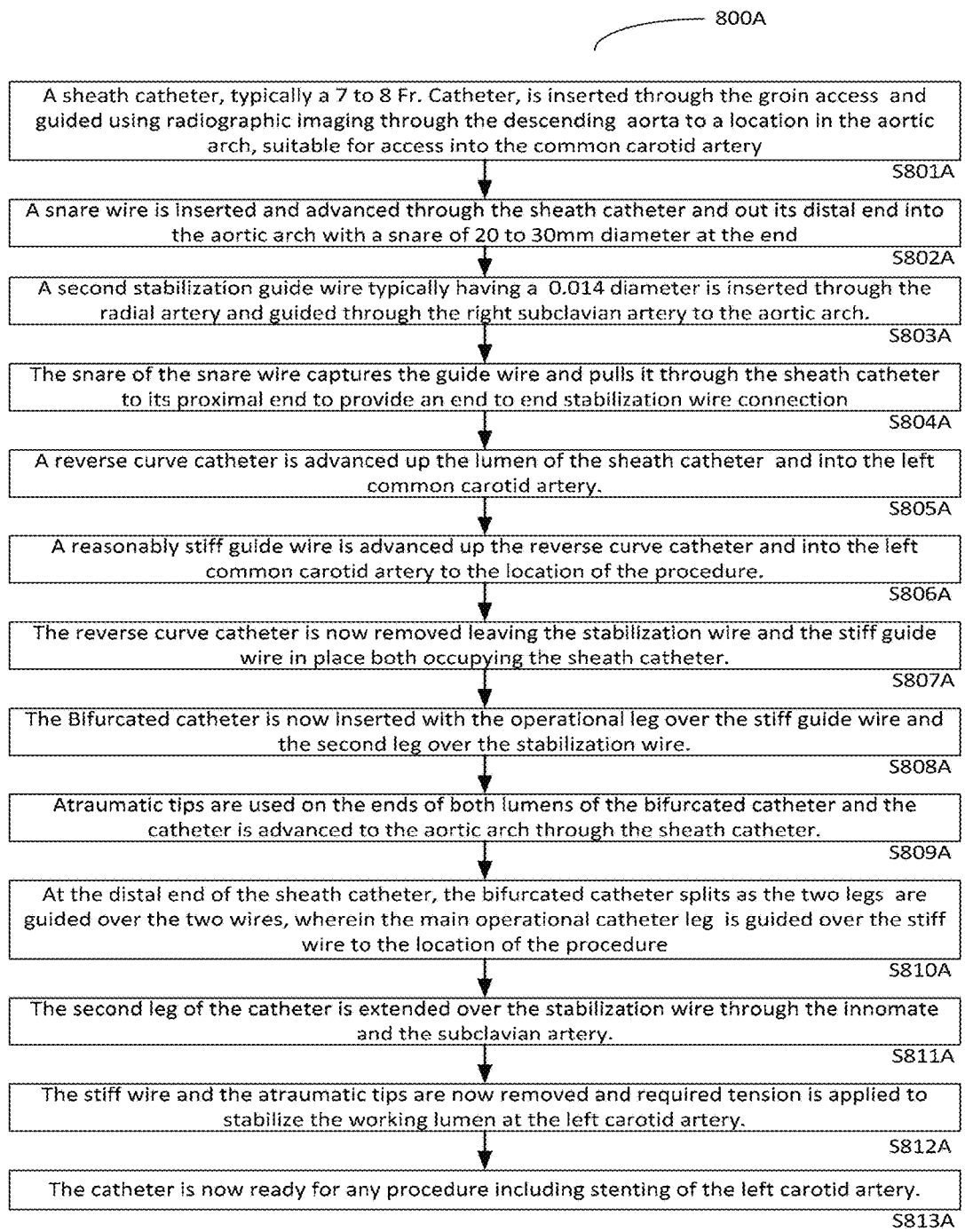
FIG. 8A is a flow chart of a procedure for stabilizing the process catheter and stenting systems in accordance with one embodiment of the invention.
Figure 8:
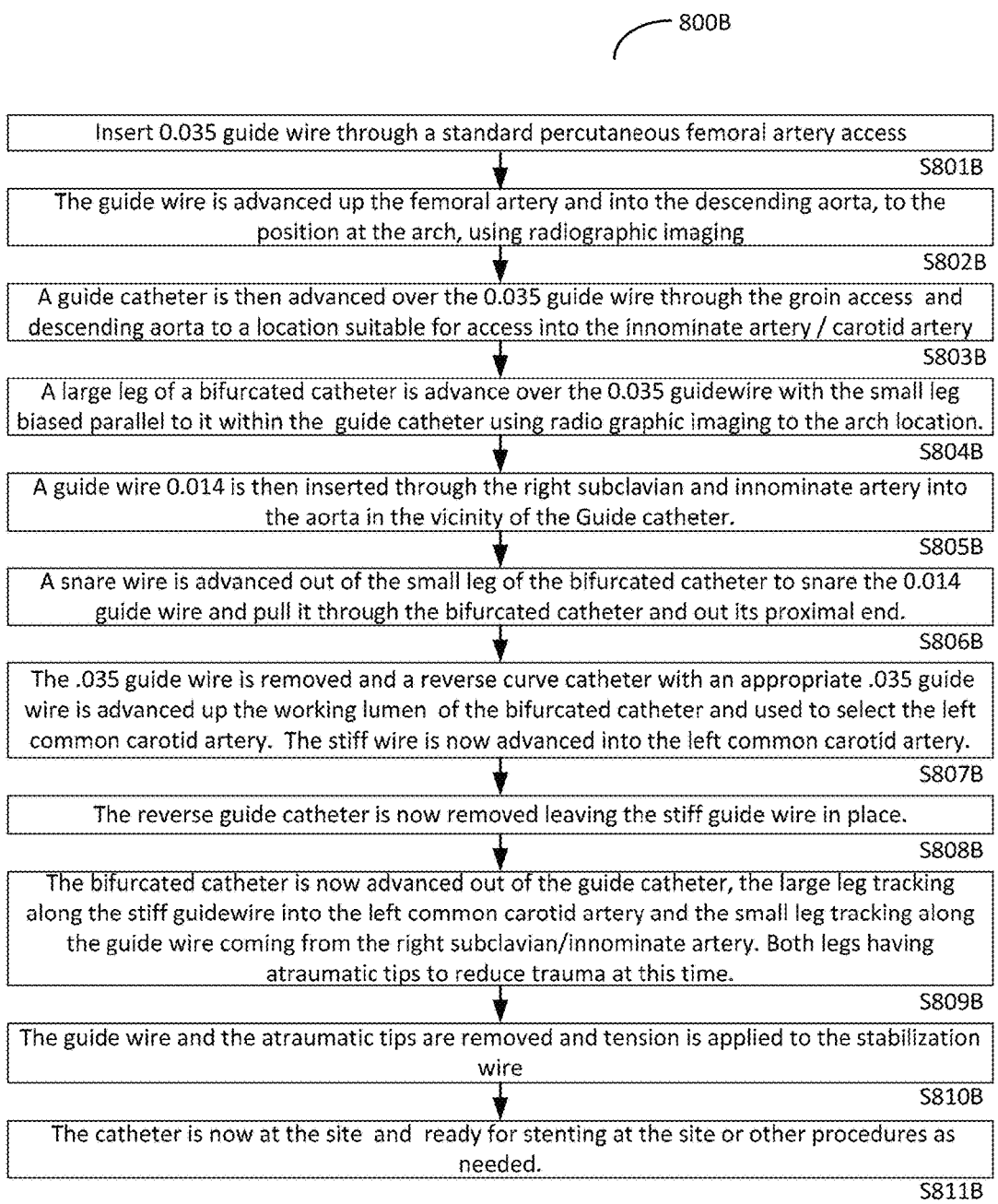
FIG. 8B is a flow chart of a procedure for stabilizing the process and stent catheters in which one of bifurcations of the pre-loaded bifurcated catheter is used to accommodate the snare/stabilization catheter in accordance with one embodiment of the invention.

FIG. 8A illustrates the process 800A described above with reference to FIGS. 2-7.

The process 800A begins by inserting a sheath catheter 18 catheter through the groin access and guided using radiographic imaging using the opaque ring 20 at its distal end through the descending aorta 12 to a location in the aortic arch 13 suitable for access into the left common carotid artery 15 (block S801A).

The process 800A continues by inserting and advancing a snare wire through the sheath catheter 18 and out its distal end into the aortic arch 13 (block S802A).

The process 800A continues by inserting a second stabilization guide wire 19 through the radial artery and guiding it through the right subclavian artery 14 to the aortic arch 13 (block S803A).

The process 800A continues by using the snare loop 21 of the snare wire to capture the guide wire 19 and pull it through the sheath catheter 18 to its proximal end to provide an end-to-end stabilization wire over which tensions can be applied (block S804A).

The process 800A continues by advancing a reverse curve catheter 24 up the lumen of the sheath catheter 18 and into the left common carotid artery 15, again using the opaque ring 25 at its distal end (block S805A).

The process 800A continues by advancing a reasonably stiff guide wire 23 up the reverse curve catheter 24 and into the left common carotid artery 15 to the location of the procedure near the left internal carotid artery 16 (block S806A).

The process 800A continues by removing the reverse curve catheter 24, leaving the stabilization wire 19 and the stiff guide wire 23 in place, both occupying the lumen of the sheath catheter 18 (block S807A).

The process 800A continues by inserting a bifurcated catheter having a main operational leg 25 over the stiff guide wire 23 and having a stabilization leg 26 over the stabilization wire 19 (block S808A).

The process 800A continues by advancing the bifurcated catheter having atraumatic tips 28 on the end of the main operational catheter leg 25 to the aortic arch 13 through the sheath catheter 18 (block S809A).

The process 800A continues by advancing the main operational leg 25 to the location of the procedure by advancing the main operational catheter leg 25 over the stiff wire 23 (block S810A).

The process 800A continues by extending the second leg 26 of the bifurcated catheter over the stabilization wire 19 through the innominate and the subclavian artery 14 (block S811A).

The process 800A continues by removing the stiff wire 23 and the atraumatic tips 28 and applying tension to the stabilization wire 19 to stabilize the working lumen leg 25 at just below the left internal carotid artery 16 (block S812A).

The process continues by performing any treatment procedure, including stenting of the left internal carotid artery 16, through the main operational catheter leg 25 (block S813A).

In another embodiment, the bifurcated catheter accommodates the snare catheter in the secondary lumen. In this embodiment, one leg 25 of the bifurcated catheter is used as the procedural catheter and the other leg of the bifurcated catheter 26 is used initially to send in the snare loop 21 and capture the stabilization wire 19. A reverse curve catheter 24 is sent through the procedural leg 25 of the bifurcated catheter into the LCCA 15 or RCCA and the stiff guide wire 23 is placed at the location of the procedure site. The second leg of the bifurcated catheter already at the aortic arch 13 is equipped with an atraumatic tip 28 and guided along the wire 23 to the location of the procedure. At the same time, the first leg 26 of the bifurcated catheter is extended to cover the stabilization wire 19 into the subclavian artery 15. The atraumatic tip 28 and the stiff wire 23 are then removed and the second leg 25 of the bifurcated catheter is ready for the next treatment steps at the site, including stenting or other procedures. This embodiment is further described with reference to FIGS. 2-7 and FIG. 8B.

In this embodiment, a bifurcated catheter is inserted with the main sheath catheter. In this embodiment, the bifurcated catheter has two chambers therein, one for the procedure and the second chamber for the snare catheter, snare loop/wire, and stabilization wire. This enables passing a snare catheter, snare loop/wire and stabilization wire all through a second chamber/branch of the bifurcated catheter when it is at the apex of the curve of the aortic arch similar to the process described earlier. The process is described below with reference to FIGS. 2-7 and flow chart 800b of FIG. 8B.

FIG. 2 illustrates the distal end of sheath catheter device 18, showing the distal end 20 of the device percutaneously inserted and advanced through the descending thoracic aorta 12 to the aortic arch 13. The bifurcated catheter (not shown) is inserted with the sheath catheter and advanced to the aortic arch 13. A snare wire with a 20 to 30 mm snare is shown extended from the sheath catheter in FIG. 2. In this embodiment, the snare is within the smaller chamber of the bifurcated catheter within the sheath catheter. The snare captures a stabilization wire 19 that is extended into the aortic arch 13 from the right subclavian artery (RSA) 14, as shown in FIG. 2. FIG. 2 further shows the ascending aorta 11, the LCCA 15, the left internal carotid artery 16 and the heart 50.

FIG. 3 shows the snare being tightened 22. In this embodiment, the snared stabilization wire 19 is pulled into the smaller lumen of the bifurcated catheter (not shown) and to the proximal end of the same to provide and end-to-end stabilization for the procedural catheter.

FIG. 4 shows a reverse curve catheter 24 such as a Simmons catheter with a stiff wire 23 being extended from the sheath catheter 18. The reverse curve catheter 24 is extended through the second, larger chamber of the bifurcated catheter into the CCA 15 and advanced to the site of the procedure at just below the left internal carotid artery 16.

The left carotid artery is shown in the figures but it is not meant to be limiting as procedures in both right and left carotid can be addressed with this implementation. Also the carotid artery may be selected with the same reverse guide catheter and a softer guidewire. Once selection has occurred the softer guidewire may be exchanged for the stiffer guidewire.

FIG. 5 shows the stiff wire/guide wire 23 being left at the intended site of the procedure after removal of the reverse catheter.

FIG. 6 shows the bifurcated catheter being advanced with the large lumen 25 over the stiff wire 23 to the site of the procedure and the small lumen 26 over the stabilization wire 19. An atraumatic tip is used to reduce trauma to the artery during this catheter advance.

FIG. 7 shows the catheter 25 with the wire and the atraumatic tips removed and ready for the procedure. Stabilization for the process catheter is provided by applying tension to the stabilization wire 19, to stabilize and fix the location of the sheath catheter and the position of the bifurcation.

FIG. 8B illustrates a process 800B for stabilizing and fixing the location of the sheath catheter and the position of the bifurcation catheter in accordance with one embodiment of the invention.

The process 800B begins by inserting a guide wire 23 through the femoral artery percutaneously (block S801B).

The process 800B continues by advancing the guide wire 23 through the descending thoracic aorta 12 to the aortic arch 13 using radiographic imaging (block 5802B).

The process 800B continues by inserting a guide or sheath catheter 18 having a platinum ring 20 that is opaque to X-ray at its distal end through the groin access and guiding the sheath catheter 18 through the descending aorta over the guide wire to the aortic arch 13 to a location suitable for access into the left common carotid artery 15 and the left internal carotid artery 16 that is being accessed for the procedure using x-ray fluoroscopy (block S803B).

The process 800B continues by inserting the larger leg of the bifurcated catheter 25 with the smaller leg 26 arranged parallel to it and guiding the bifurcated catheter over the guide wire 23 to the distal edge 20 of the sheath catheter 18 (block S804B).

The process 800B continues by inserting a stabilization guide wire 19 through the brachial artery preferably using a micro sheath and advancing the stabilization guide wire 19 through the right subclavian artery 14 into the aortic arch 13 (block S805B).

The process 800B continues by extending a second segment of the stabilization guide wire having a snare 21 at its distal end out of the smaller leg 26 of the bifurcated catheter to capture the stabilization wire 19 from the subclavian artery and pull it through the smaller leg of the bifurcated catheter and out to its proximal end providing an end to end stabilization wire for stabilizing the sheath and the bifurcated catheter (block S806B).

The process 800B continues by advancing a reverse guide catheter 24 through the tortuous connection of the left common carotid artery 15 to the aorta at the aortic arch 13 over a reasonably stiff wire 23 up the working lumen of the larger leg of the bifurcated catheter through the left common carotid artery 15 just below the left internal carotid artery 16 where the procedure is to be carried out (block S807B).

The process 800B continues by removing the reverse guide catheter 24 and leaving the stiff guide wire 23 in place as a guide to the bifurcated catheter (block S808).

The process 800B continues by advancing the bifurcated catheter out of the guide catheter, the large leg 25 of the bifurcated catheter tracking along the stiff guide wire 23 into the left common carotid artery 15 and the small leg 26 tracking along the guide wire 19 coming from the right subclavian/innominate artery (block S809).

The process 800B continues by removing the guide wire 23 and the atraumatic tips 28 and applying tension to the stabilization wire 19 to stabilize the main catheter leg 25 extending to just below the left internal carotid artery 16 (block S810).

The process 800B continues by performing a treatment procedure, such as stenting or other procedures as needed, at the treatment site (block S811).

FIGS. 9 to 15 and FIG. 16 illustrate another embodiment of the invention in which a modified snare bifurcated sheath with a side hole is used instead of the bifurcated catheter to provide stability to the procedural catheter used for stenting and other procedures in the carotid arteries. In this embodiment, the snare loop is inserted through the subclavian artery to capture the snare wire and provide a through-and-through capability for stabilization of the procedural catheter. In some embodiments, the snare loop is inserted through the subclavian artery via a right radial or brachial artery access.

Figure 9:
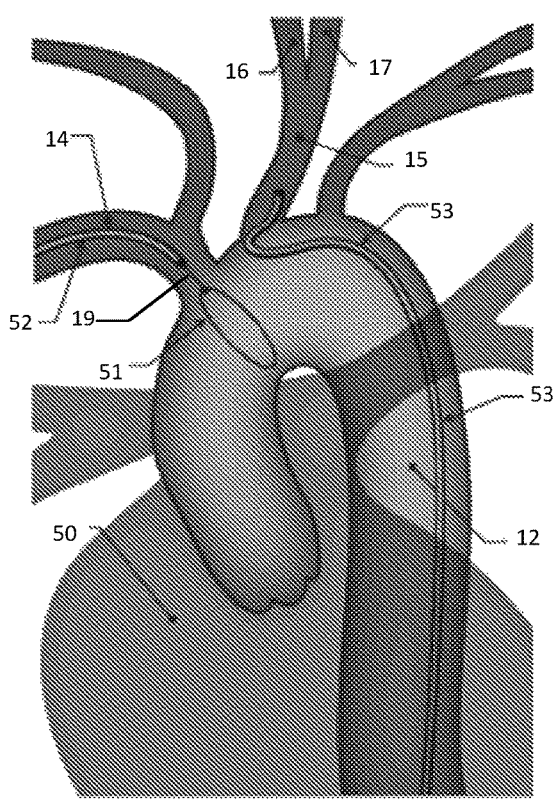
FIG. 9 is a schematic diagram showing the snare wire extended from a protective sheath through the subclavian artery (AS) in accordance with one embodiment of the invention.

FIG. 9 shows a snare wire 19 having a snare loop at its distal end inserted through the radial artery using a sheath 52 extended through the right subclavian artery 14 into the aortic arch 13. In one embodiment, the sheath 52 is a Fr 5 sheath. In one embodiment, the snare loop 51 has a 30 to 40 mm diameter. A reverse curve catheter 53, such as a Simmons catheter, is inserted through the groin access and guided through the descending aorta 12 to select the left common carotid artery 15 (it can also be used to select the right carotid artery). In one embodiment, the reverse curve catheter 53 is a Fr. 5 catheter.

Figure 10:
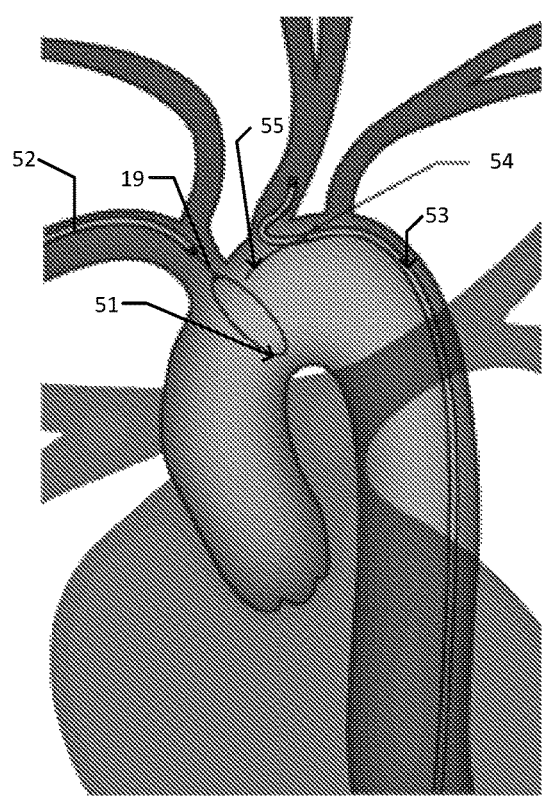
FIG. 10 is a schematic diagram showing a wire extended out of a side hole of the initial reverse curve diagnostic catheter to be captured by the snare in accordance with one embodiment of the invention.

FIG. 10 further shows a secondary stabilization wire 55 that is inserted from the proximal end of the reverse curve catheter 53 and exited out of a hole 54 on the side of the catheter 53 at the location at the apex of the curve of the aortic arch 13. In one embodiment, the secondary stabilization wire has a 0.014 diameter.

FIG. 11 shows the stabilization wire 55 being snared by the snare 56 to provide a tensionable stabilization capability comprising the snare 56 from the sheath catheter 52 coming from the right subclavian artery and the snared wire 55 coming from the reverse curve catheter 53.

FIG. 12 further shows a stiff guide wire 57 being extended from the reverse catheter 53 into the left common carotid artery 15 and below the left internal carotid artery 16 where the procedure is expected to be carried out once the tensionable stabilization is established.

Figure 13:
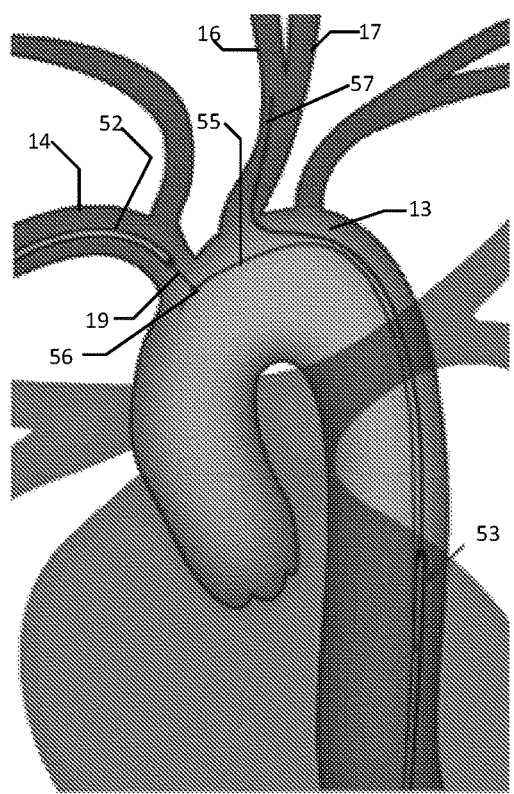
FIG. 13 is a schematic diagram showing the removal of the reverse catheter leaving the guide wire and the stabilization wire in place in accordance with one embodiment of the invention.

FIG. 13 shows the withdrawal of the reverse catheter 53 leaving both the snare 56, snared stabilization wire 55, and the stiff guide wire 57 into the left common carotid artery 15, and below the left internal carotid artery 16.

Figure 14:
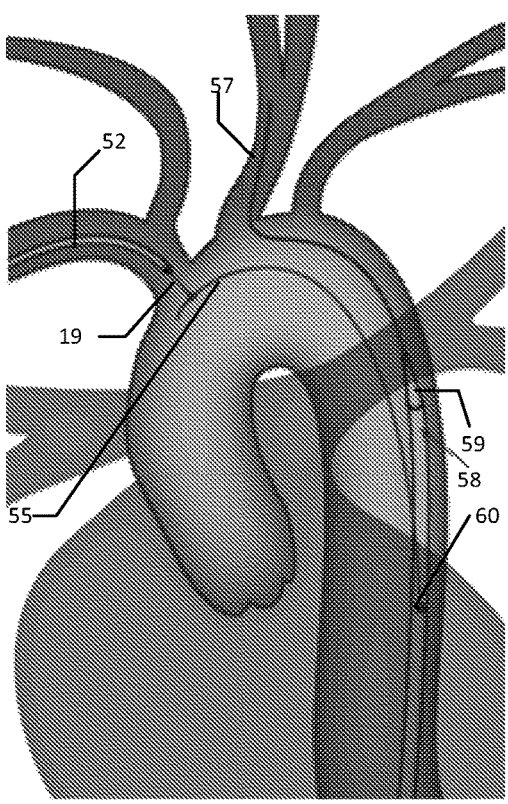
FIG. 14 is a schematic diagram of the working sheath catheter, having an atraumatic tip and the working sheath catheter having a second chamber for the guide wire extending out of a side hole, being advanced over the guide wire in accordance with one embodiment of the invention.

FIG. 14 shows a bifurcated sheath catheter 58 having two chambers—one for the stabilization wire and the other for the process catheter with an atraumatic dilator tip 59, being guided over the stiff guide wire and the stabilization wire 55, which exits the sheath through a hole 60, in the sheath catheter 58. In one embodiment, the bifurcated sheath catheter 58 is a Fr. 6 or Fr. 7 sized catheter.

Figure 15:
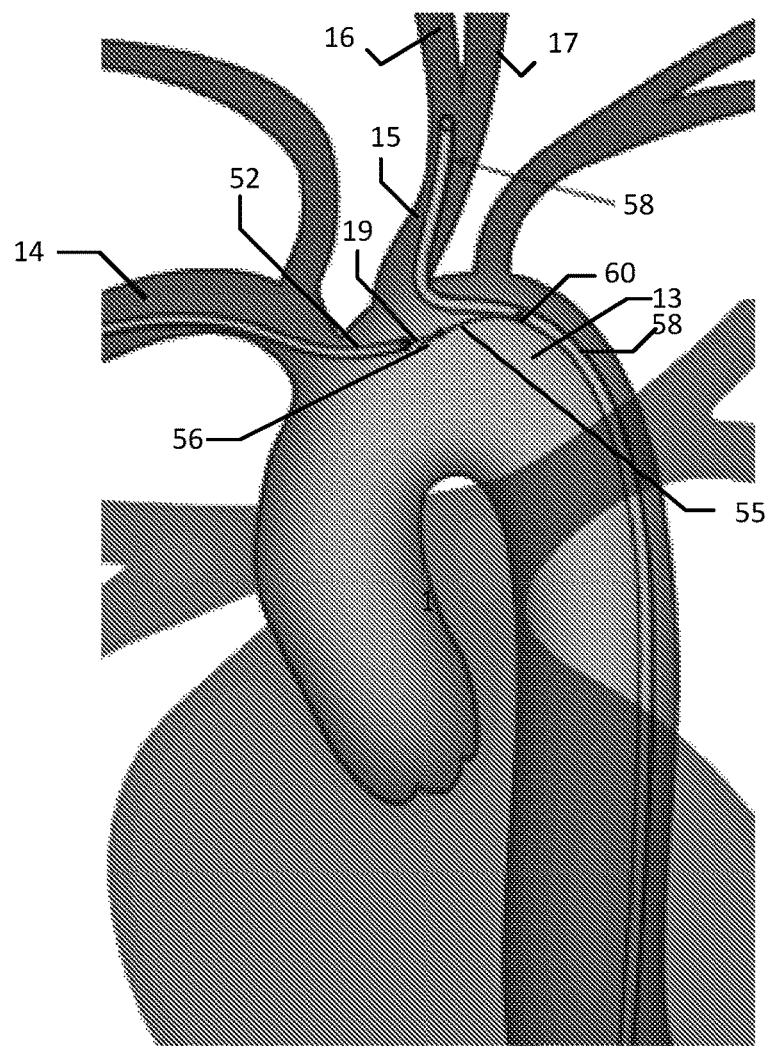
FIG. 15 is a schematic diagram of the working sheath catheter advanced to the location of the procedure and the guide wire removed in readiness for a procedure in accordance with one embodiment of the invention.

FIG. 15 shows the sheath catheter 58 with the stiff wire and atraumatic tip removed with the snared stabilization wire 55, forming an end-to-end wire enabling stabilization tension to be applied to stabilize the sheath catheter 58 extending into the left internal carotid artery 16 for inserting the procedural catheter for stenting and other procedures from the aortic arch 13.

In yet another embodiment, the initial sheath catheter may have two lumens, one for the support and stabilization wire and a second as the operational catheter. Further, the operational catheter may be made with a softer operational leg at its distal end which can be used as a reverse curve guiding catheter as well. By combining the application capabilities of such a catheter, it is possible to reduce the number of catheters used and hence the number of steps needed for set up and completion of the procedure.

Figure 16:
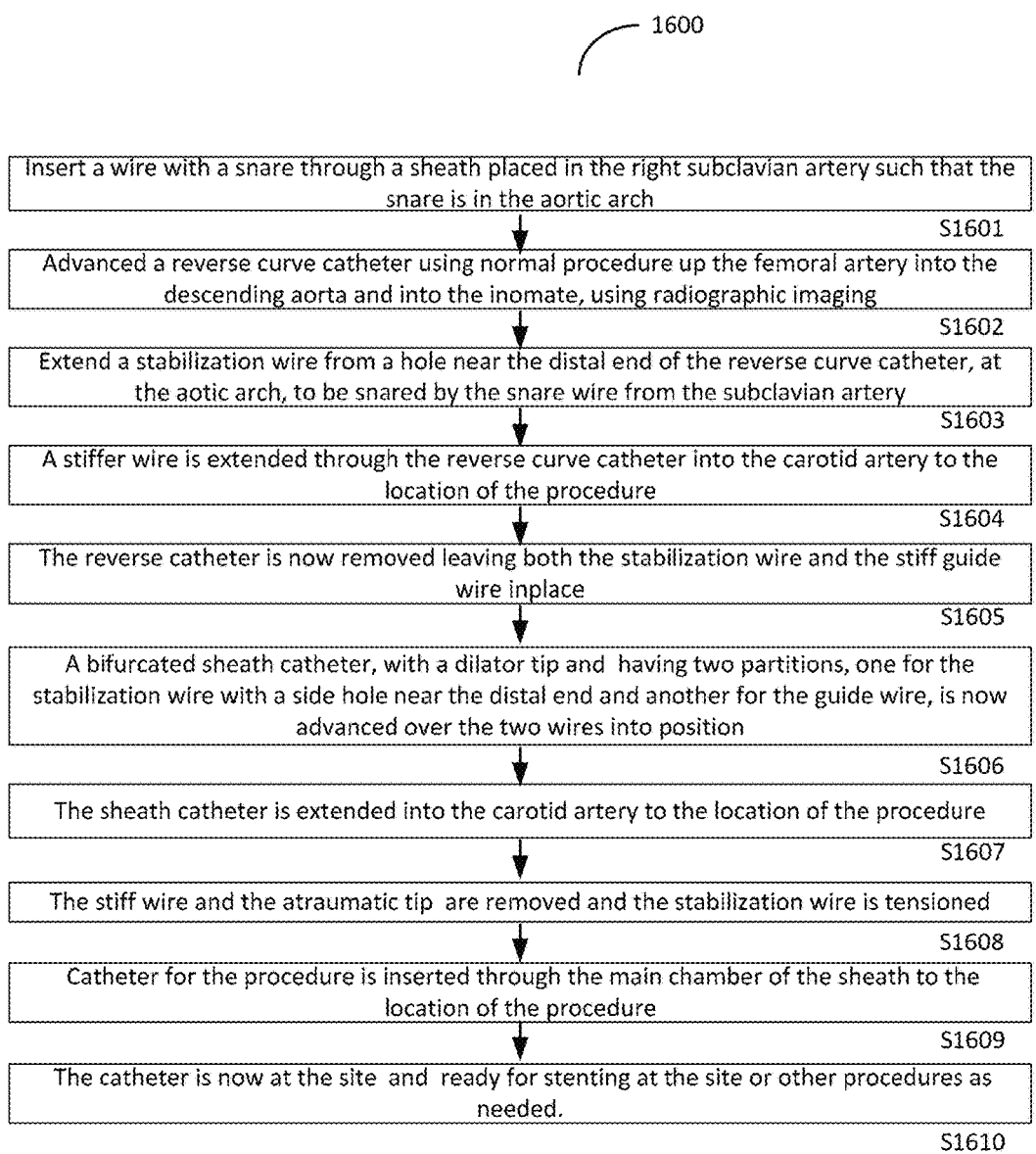
FIG. 16 is a flow diagram for stabilizing the process catheters and systems in accordance with one embodiment of the invention.

FIG. 16 is flow chart illustrating a process 1600 according to another embodiment of the invention.

The process 1600 begins by inserting a wire with a snare 51 through a sheath 52 that is inserted through the radial artery and directed through the right subclavian artery 14 such that the snare is in the aortic arch 13 (block S1601).

The process 1600 continues by percutaneously inserting and advancing a reverse curve catheter 53 up the femoral artery into the descending thoracic aorta 12 into the left common carotid artery 15 using radiographic imaging (block S1602).

The process 1600 continues by inserting a secondary stabilization wire 55 into the reverse curve catheter 53 at the proximal end and exited from a hole 56 near the distal end of the reverse curve catheter at the aortic arch 13 to be snared by the snare 51 from the subclavian artery 14 (block S1603).

The process 1600 continues by snaring the stabilization wire 55 to provide an end to end stabilization (55) to the catheter, and extending a stiff guide wire 57 through the reverse curve catheter 53 into the left common carotid artery 15 to the location of the procedure (block S1604).

The process 1600 continues by removing the reverse curve catheter 53, leaving both the stabilization wire 55 and the stiff guide wire 57 in place in the arteries (block S1605).

The process 1600 continues by advancing a bifurcated sheath catheter 58 having two partitions (one for the stabilization wire 55 with a side hole 60 near the distal end and another with a dilator tip 59 for the guide wire 57) over the two wires into position such that the sheath catheter for process 58 is extended into the carotid artery 16 while the stabilization wire 55 through the hole 60 in the bifurcated sheath catheter 58 extends from the proximal end of the sheath catheter 58 through the hole 60, through the aortic arch 13 and subclavian artery 14 to provide a through and through capability to provide tension and stabilization to the operating catheter 58 (block S1606).

The process 1600 continues by extending the sheath catheter into the left internal carotid artery 16 to the location of the procedure (block S1607).

The process 1600 continues by removing the stiff guide wire 57 and the atraumatic dilator tip 58 and tensioning the stabilization wire 55 to provide stability to the sheath catheter 58 (block S1608).

The process 1600 continues by inserting the catheter for the procedure through the main chamber of the sheath 58 to the location of the procedure in the left internal carotid artery 16 (block S1609).

The process 1600 continues by performing a stenting or other procedure at the treatment site (block S1610).

In another embodiment, a reverse curve catheter with a lumen sufficiently large for stenting instead of a sheath catheter may be used. In this embodiment, the reverse curve catheter having two lumens, one large procedural lumen and the other a smaller stabilization lumen, is used to select the carotid artery. A secondary wire is inserted in the reverse curve catheter (through the stabilization lumen) and out of a hole in the reverse curve catheter at the location of the arch. This secondary wire is then captured by a snare wire with a loop that is extended out of a protective sheath extended through the subclavian artery. The carotid stenting procedure can now proceed in the standard way using the procedural lumen of the reverse curve catheter since the reverse curve guiding catheter itself is stabilized and is usable for procedure.

Figure 17:
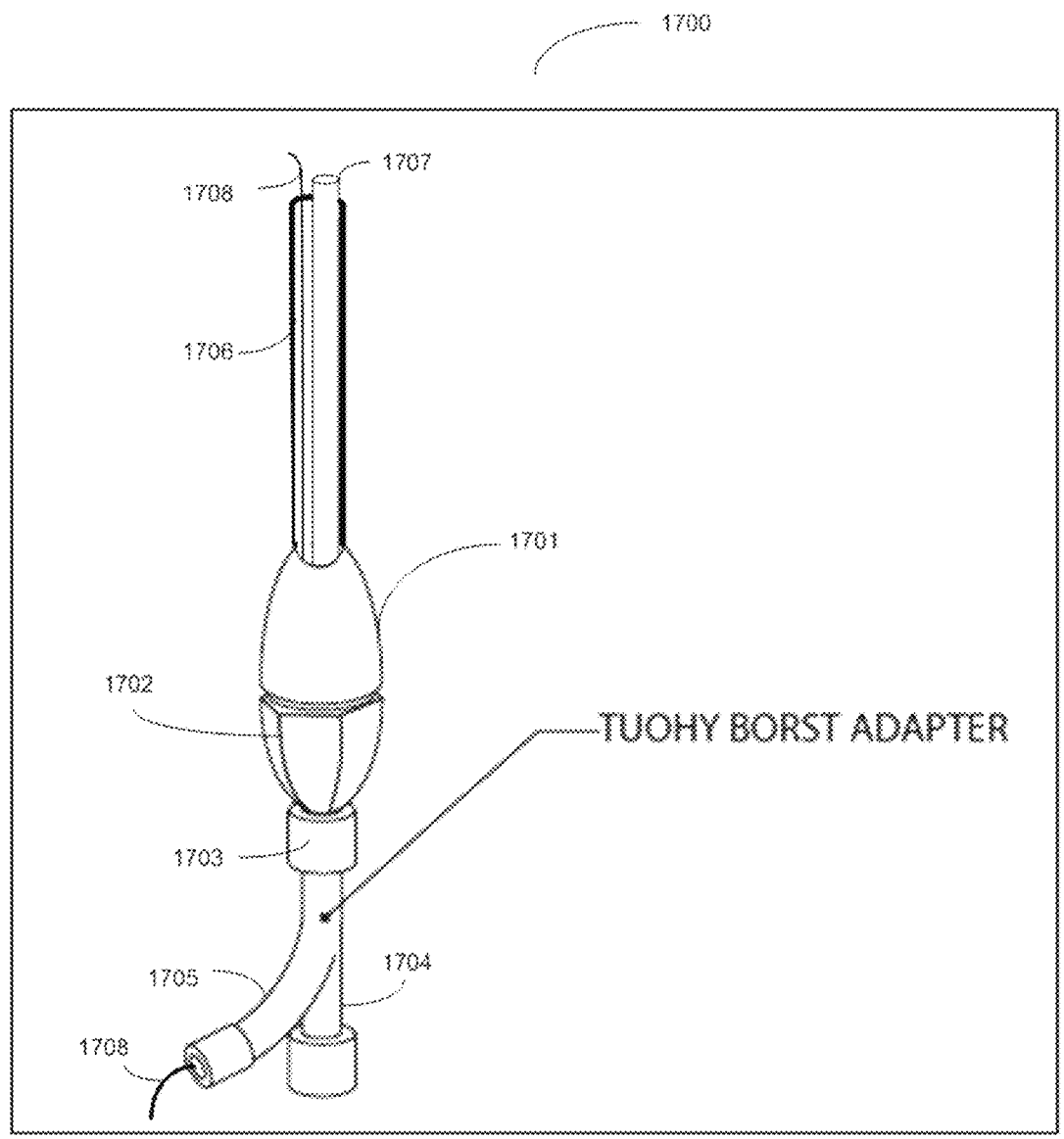
FIG. 17 is a corrective solution for leakage when using twin catheters sheaths or a catheter and a snare wire, by using a Touchy Borst Adapter of the correct size to prevents the possible leakage problem in accordance with one embodiment of the invention.

Yet another implementation or embodiment is the use of two catheters or a catheter and a snare wire within a single sheath, as shown in FIG. 17, for providing the necessary stabilization to the catheter used for the procedure. In the first embodiment, the second catheter contains the snare wire that will be used to capture the stabilization wire and provide the necessary stabilization to the catheter used for the procedure. Alternately, the snare wire and a catheter are in a single sheath. Though this twin catheter or the catheter 1707 and snare wire 1708 may provide a solution it comes with a plurality of problems. In the case where two catheters are used, there is need for a larger sheath which will accommodate the twin catheters. In many cases, it is not practical to use such a large sheath. In using twin catheters or a catheter 1707 and a snare wire 1708, there is a possibility for entanglement and twisting of the two independent catheters or the catheter 1707 and the wire 1708. This can cause difficulty in proper insertion to the site as well as during extraction of the catheter 1707 after the procedure. Also, in these cases, there is a possibility of blood leakage from the access site, as is well understood by the surgeons. In order to prevent the blood leakage, a Tuohy Borst adapter as shown in FIG. 17 is used. One access 1704 is made to fit the exact size of the catheter 1707 and the other access 1705 is used to isolate the snare wire used as shown. The Tuohy Borst adapter of FIG. 17 is attached by the adapter 1703 to a catheter handle 1702/1701 combination. The handle has a fixed holder portion 1701 connected to a manipulator section 1702.

The typical implementation of the embodiment having dual catheters without the Tuohy Borst adapter, due to the problems discussed, is not an optimum solutions and is not recommended over the more optimum solutions disclosed. Another solution is the use of the procedural catheter 1707 and a snare wire 1708 within the same sheath 1706. This solution also has the major problem of entanglement of the wire with the catheter, as the wire used is much lighter and less rigid than the catheter, with the associated problems of insertion and extraction as well as the problem of blood leakage as discussed previously. Hence, this is also not a recommended solution. As an example, the procedure may be performed using a long 8 French 70 cm sheath with a coaxial longer 6 French 90 cm catheter and a 0.18 or 0.14 inch snare wire. In this case, the procedure would be complicated by potential wire wrap of the 0.018 inch wire around the 6 French catheter causing entanglements. Furthermore, there would be persistent leakage of blood at the 8 French sheath valve, similar to the twin catheter case, which has both the 0.018 inch wire and 6 French catheter. This can be life threatening.

Figure 17A:
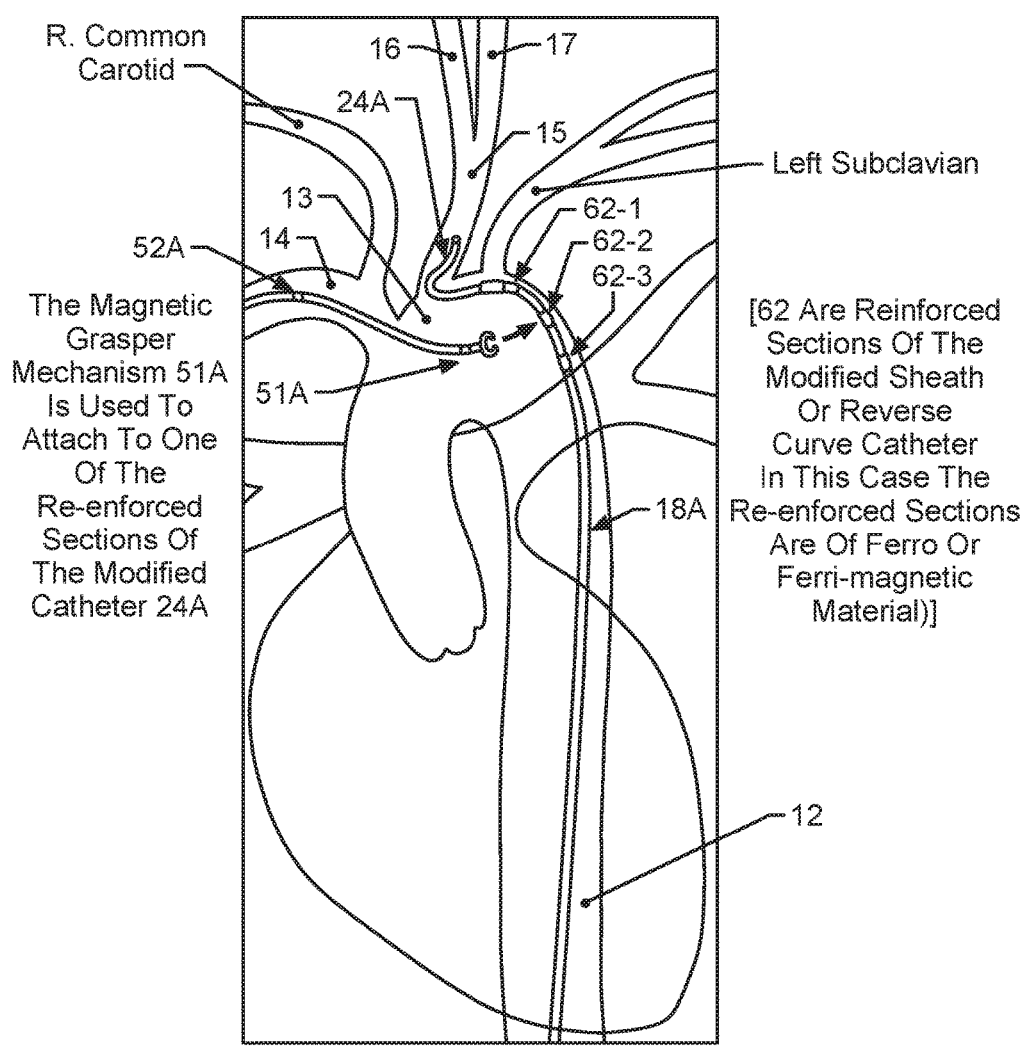
FIG. 17A illustrates a solution to provide stabilization to the procedural catheter or sheath in accordance with one embodiment of the invention.

Another way to provide stabilization to the procedural catheter or sheath is shown in FIG. 17A. Here a modified sheath/reverse curve guide catheter 24A is percutaneously inserted and advanced up the femoral artery through the descending thoracic aorta 12 into the aortic arch 13, using radiographic imaging as described previously. The modified sheath catheter 18A is reinforced with graspable sections 62 for example: 62-1, 62-2 and 62-3 shown at the appropriate locations using ferro-magnetic material. A second stabilization catheter 52A with a magnetic gripper 51A that is a latching mechanism is now introduced into the aortic arch 13 using right subclavian artery 14 access via radial or brachial artery. The magnetic latching mechanism attaches to one of the graspable reinforced ferro-magnetic sections 62 of the modified sheath catheter 18A to provide stabilization to the modified sheath catheter 18A. A reverse curve catheter 24A is now used to access the left common carotid artery 15 through the stabilized modified sheath catheter 18A as described previously for establishing a path for the procedural catheter and for conducting the procedure as described previously.

In certain embodiments the modified sheath catheter 18A may be replaced by the reverse curve guide catheter 24A having the required modifications and reinforcements for the gripper or latching mechanism to engage with it directly.

In certain other embodiment the gripper or latching mechanism is not magnetic, but is a mechanical attach mechanisms that attaches to or grips the reinforced portion of the sheath catheter 18A.

Though embodiments the invention has been described mainly as being applicable to the tortuous arterial procedures above the neck, it should not be considered limiting. The bifurcated sheath can be modified to treat contralateral lower extremity peripheral arterial disease with a complex or hostile aortic bifurcation (due to a fixed and narrow aortic bifurcation, iliac stenosis, ectasia, or tortuosity, aneurysm of the distal aorta, previous iliac stenting, previous endovascular aneurysm repair and previous aortofemoral/aortoiliac bypass grafting) using bilateral groin access. It can also be useful for renal and other visceral interventions such as renal and SMA stenting and cancer hepatic embolizations and splenic arterial interventions (using groin and radial artery access). The advantage of this device is that it can conquer adverse tortuous anatomy by providing stabilization during procedures in adverse tortuous anatomy for minimally invasive procedures through both venous or arterial access.

The use of disclosed bifurcated sheath, the dual sheath/catheter, or catheter and stabilization wire, for in treatment of contralateral lower extremity peripheral arterial disease with a steep aortobifemoral bypass graft (using bilateral groin access), renal and other visceral interventions such as renal and SMA, stenting and cancer hepatic embolizations, and splenic arterial interventions (using groin and radial artery access) are disclosed. Two examples of such use are discussed below.

Figure 18:
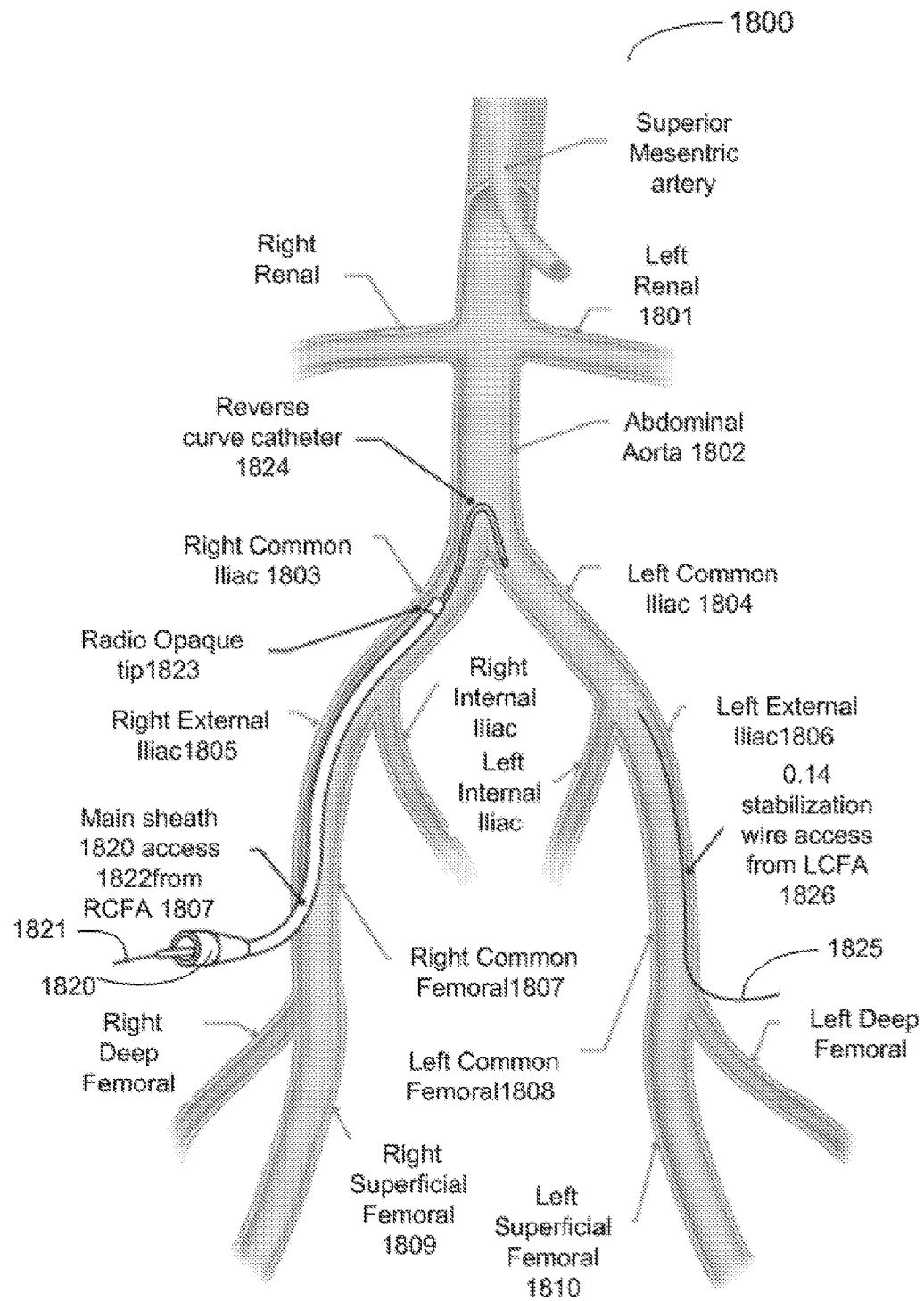
FIG. 18 is a pictorial representation of the initial step of inserting a main sheath and a reverse curve catheter from the right common femoral artery to access the left common iliac artery and introducing a stabilization wire from the left common femoral artery in accordance with one embodiment of the invention.
Figure 19:
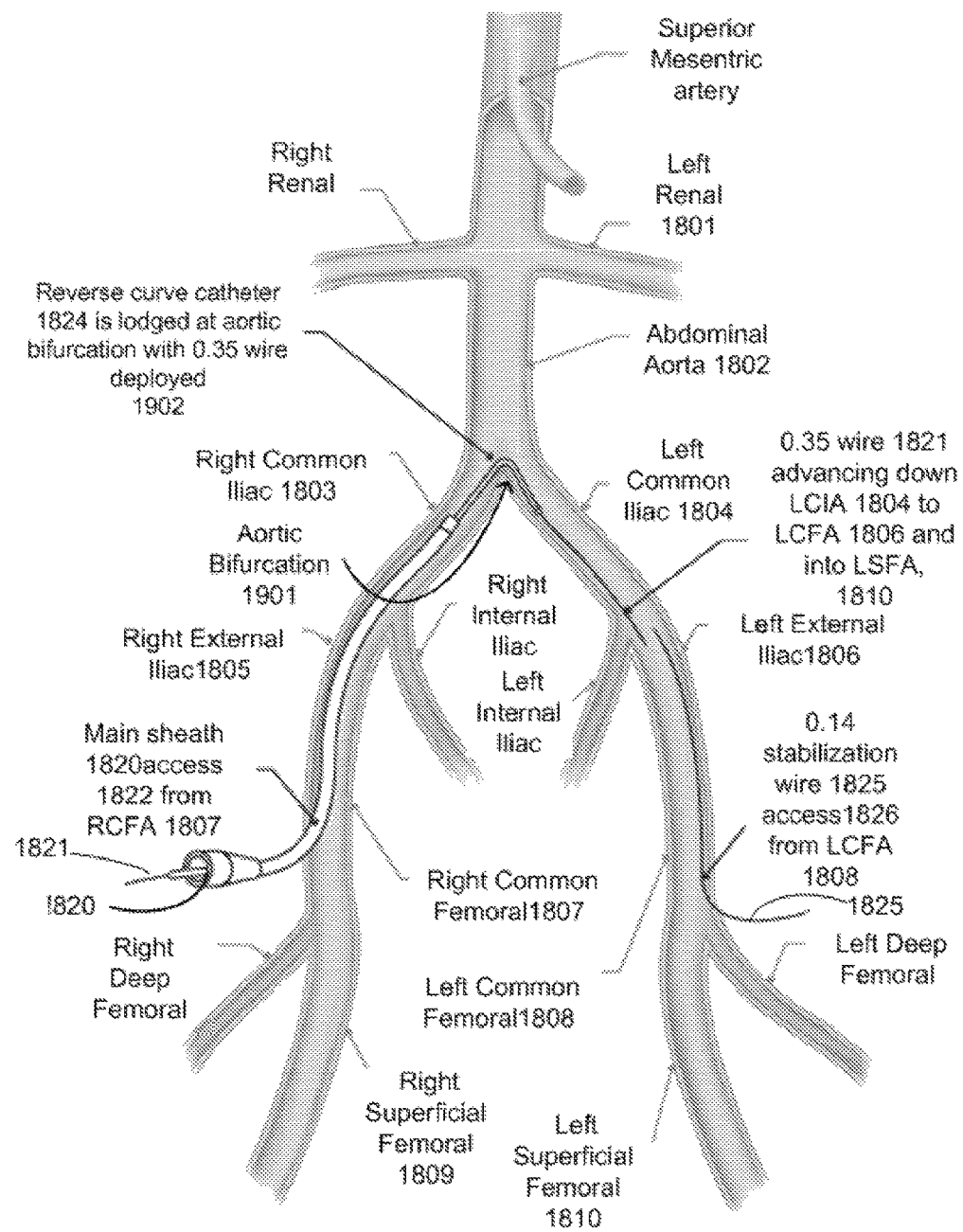
FIG. 19 is a pictorial representation of establishing a thick guide wire into the left common Iliac in accordance with one embodiment of the invention.
Figure 20:
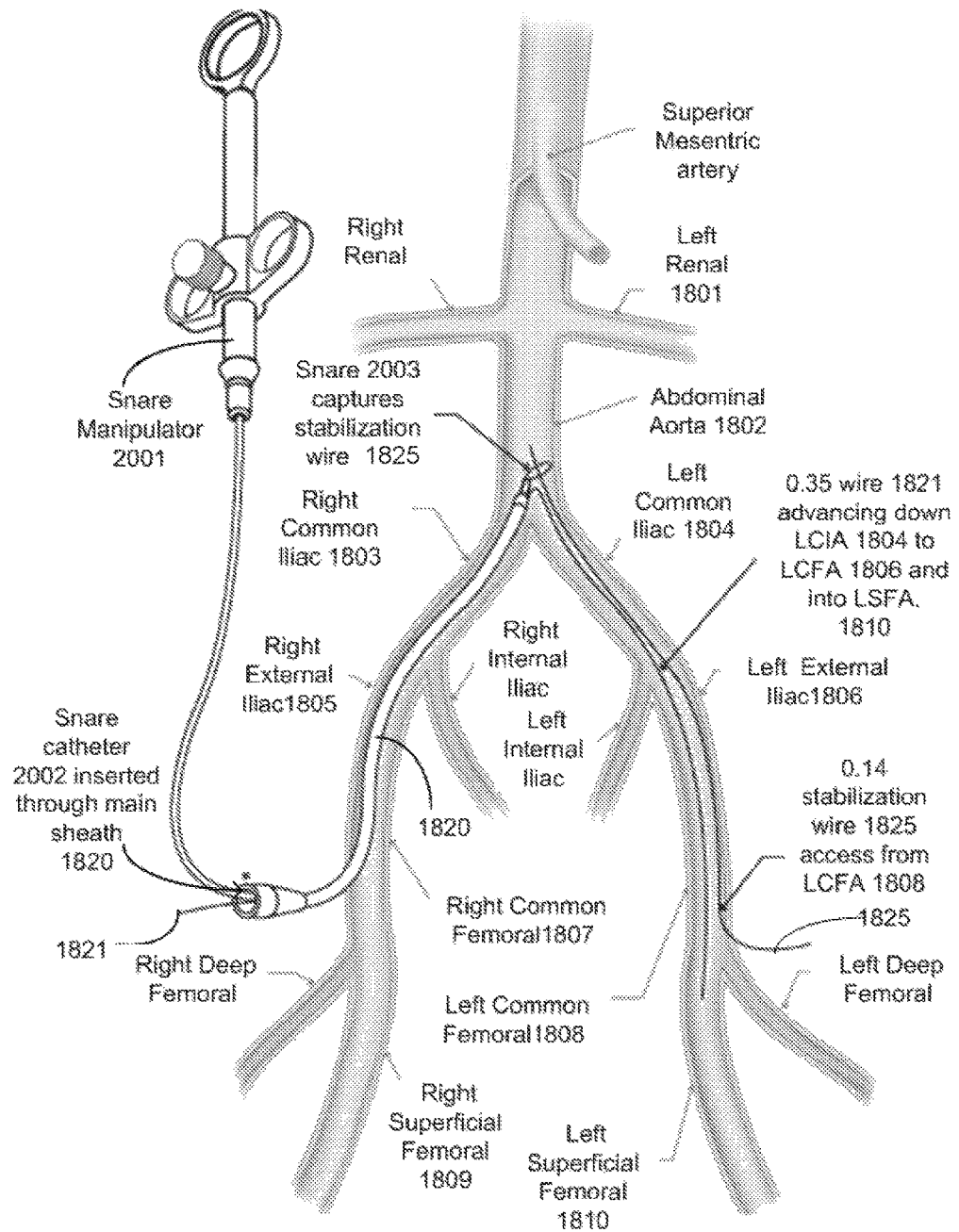
FIG. 20 is a pictorial representation of the snaring of the stabilization wire by a snare inserted through the main sheath while the thick guide wire is extended down the left superficial femoral artery in accordance with one embodiment of the invention.
Figure 21:
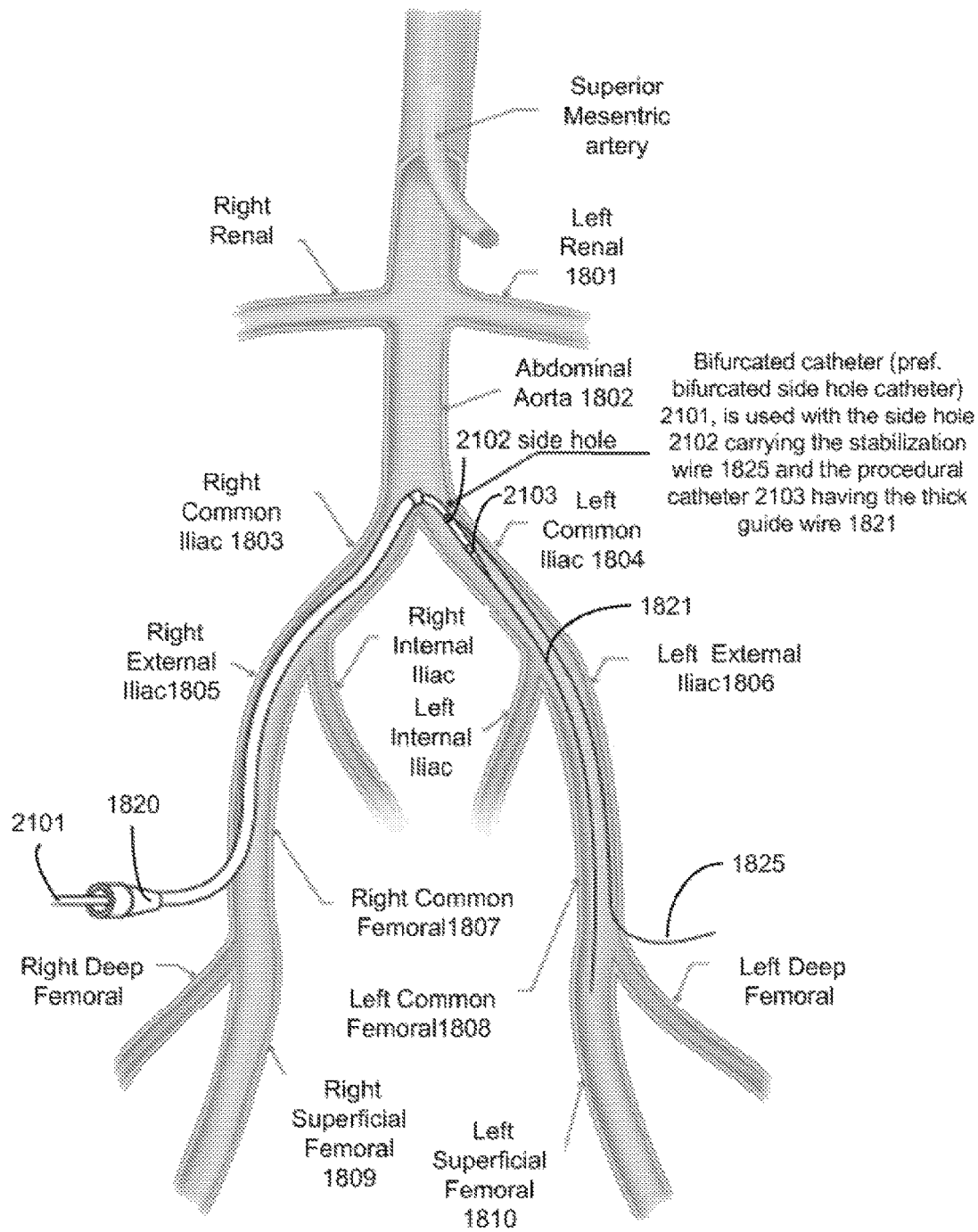
FIG. 21 is a pictorial representation of introduction of the bifurcated catheter (the side hole catheter) through the main sheath over the thick guide wire while the stabilization wire is carried through the side hole of the bifurcated side hole catheter in accordance with one embodiment of the invention.
Figure 22:
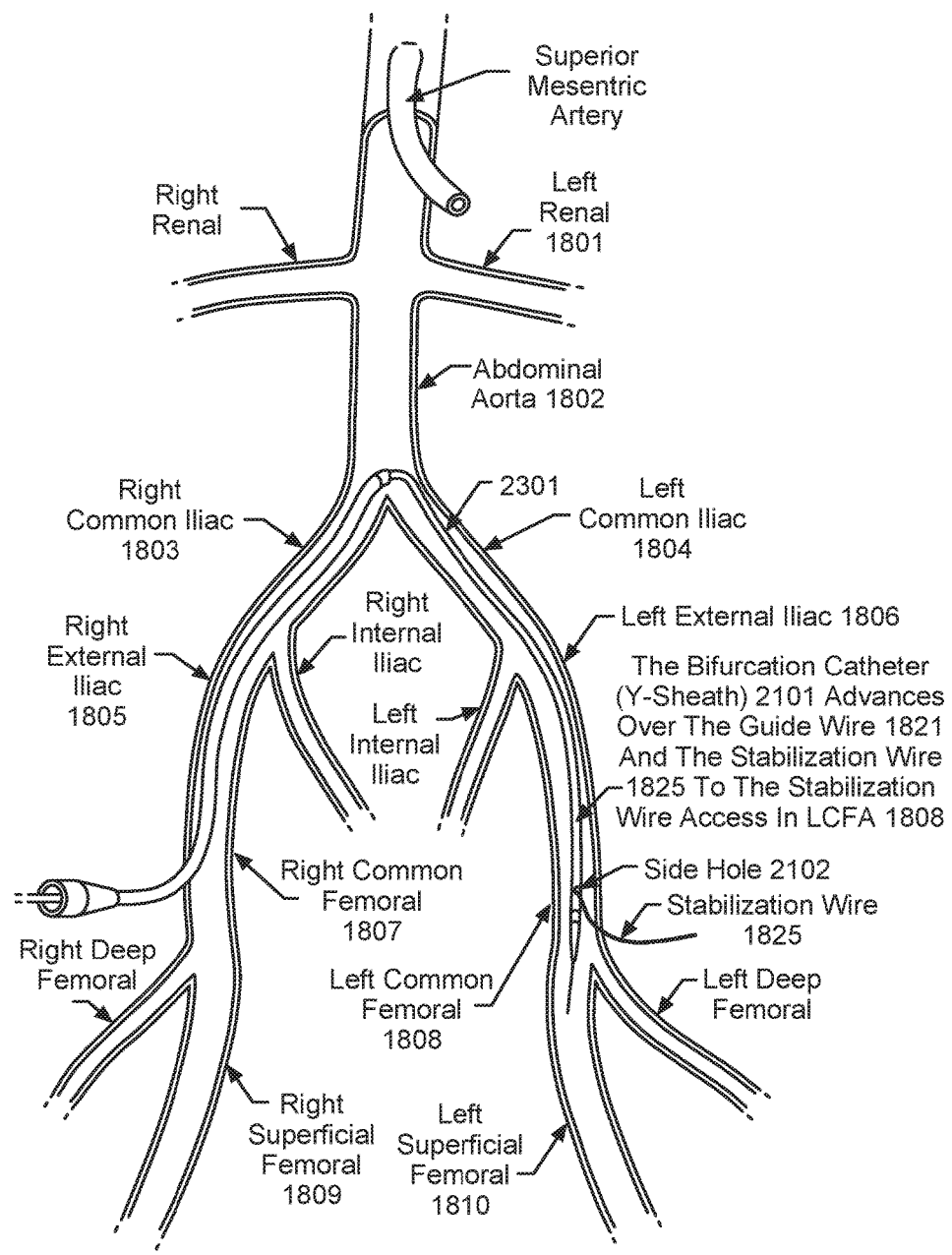
FIG. 22 is a pictorial representation of the bifurcated catheter with the bifurcation/side hole at the access point of the stabilization wire providing end to end stabilization for the procedural catheter which is extending into the left superficial femoral artery in accordance with one embodiment of the invention.
Figure 23:
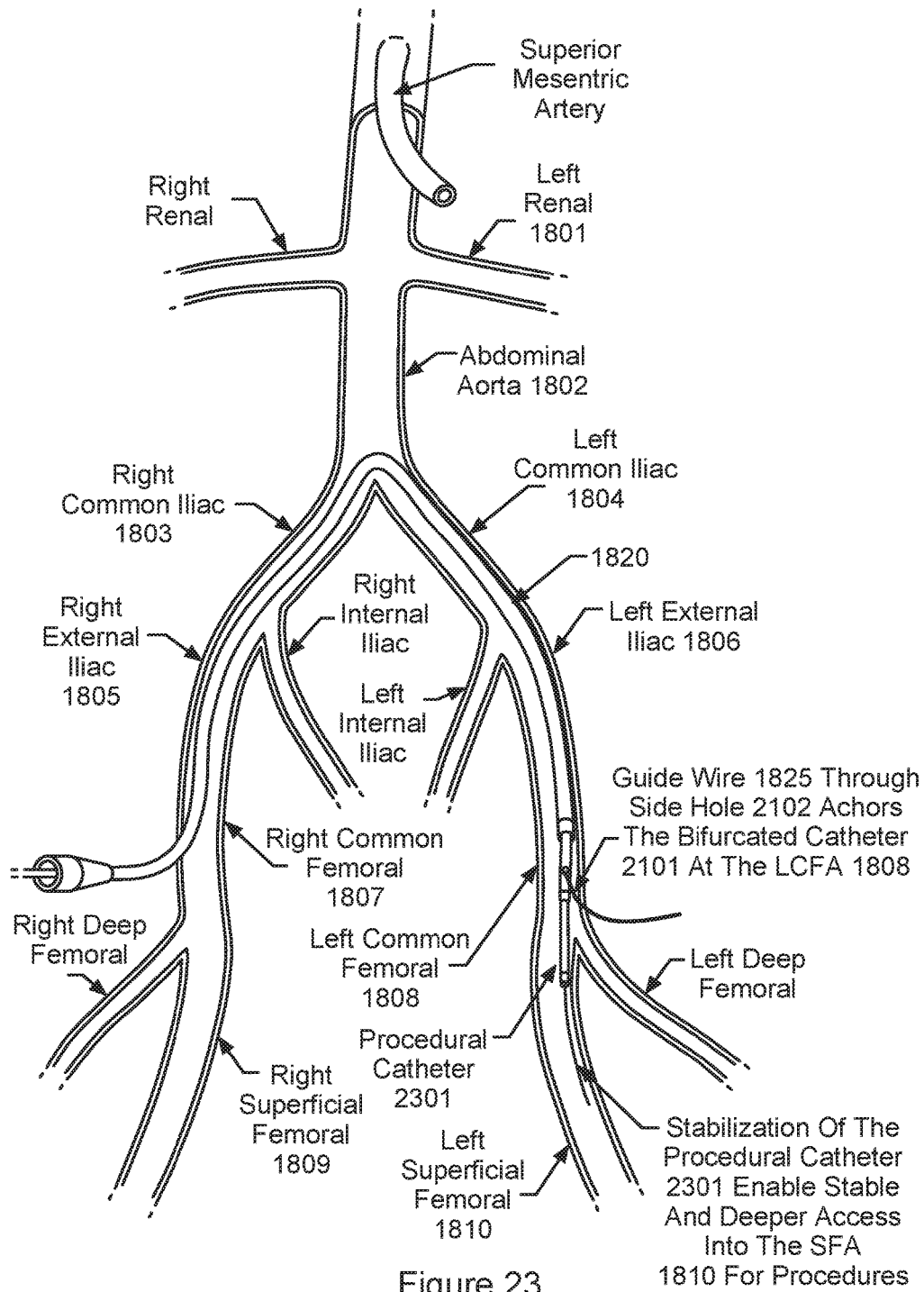
FIG. 23 is a pictorial representation of the main sheath being extended to the side hole location of the bifurcated catheter to improve stability of the procedural catheter while the procedural catheter from the bifurcated catheter extending into the left superficial artery ready for aorto-bifemoral bypass application in accordance with one embodiment of the invention.
Figure 24:
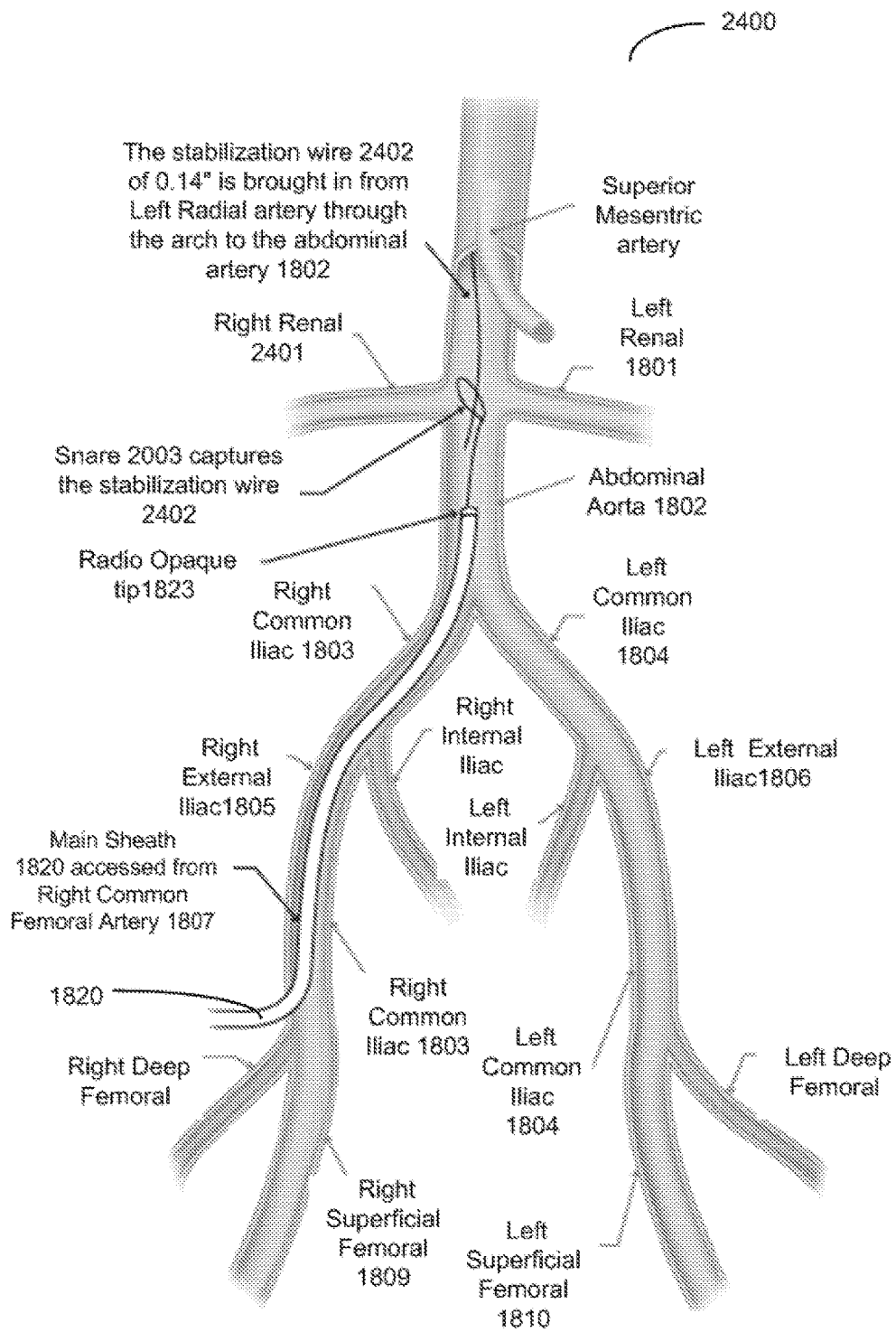
FIG. 24 is a pictorial representation of inserting a main sheath from the right common femoral artery with a snare that is used to capture the stabilization wire from left radial artery in accordance with one embodiment of the invention.

FIGS. 18-23 show the exemplary use of the bifurcated catheter with a side hole (the side hole catheter) for stabilization of the procedural catheter in Aorto Bifemoral Bypass application. The figures identify the main arterial branches that are involved—the left renal artery 1801 goes off the abdominal Aorta 1802. The abdominal aorta 1802 bifurcates into the right iliac 1803 and the left iliac 1804 both of which continue as right external iliac 1805 and left external iliac 1806 after the right and left internal iliacs go off the right iliac 1803 and left iliac 1804. As they transition down the body the right external iliac continues as the right common femoral artery 1807 and the left external iliac continues as the left common femoral artery 1808 which further down becomes the right superficial femoral 1809 and the left superficial femoral artery 1810. During aorto bifemoral bypass application as shown in FIG. 18 the main sheath 1820 access 1822 is made through the right common femoral artery 1807 and stabilization wire 1825 of 0.14" access 1826 through the left common femoral artery 1808. As shown in FIG. 18 and FIG. 19 the main sheath 1820 is extended into the right common iliac 1803, close to the aortic bifurcation 1901 and a reverse curve catheter 1824 with a thick guide wire 1821, typically of 0.35", is inserted through the sheath 1820 and placed at the bifurcation 1901 as shown at 1902 to gain access to the left iliac 1804. The thick guide 1821 is now extended down the left iliac 1804 to the left common femoral artery 1808. FIG. 20 shows the introduction of a snare catheter 2002 using a snare manipulator 2001 into the main sheath to have a snare 2003 at the aortic bifurcation 1901. The snare 2003 is used to capture the stabilization wire 1825 and pull it into and out of the main sheath 1820 at the proximal end, to create an end to end stabilization capability. In FIG. 21, the reverse curve catheter 1824 is now removed and a bifurcated 'Y' or side hole sheath catheter 2101 is introduced through the main sheath 1820 with the thick guide wire 1821 through the larger arm of the 'Y' catheter 2101 and guided over the thick guide wire 1821 such that the side hole 2102 of the bifurcated catheter 2101 is at the access point on the LCFA 1808 of the stabilization wire 1825. The side hole of the bifurcated catheter 2101 carries the stabilization wire 1825. FIG. 22 shows the main sheath 1820 extended over the bifurcated catheter 2101 to the access point of the stabilization wire 1825, through the LCFA 1808. FIG. 23 shows the use of the stabilization wire 1825 to anchor and stabilize the procedural catheter 2301 so that deeper penetration in a stable way is made possible for procedures in the LSFA 1810.

Figure 25:
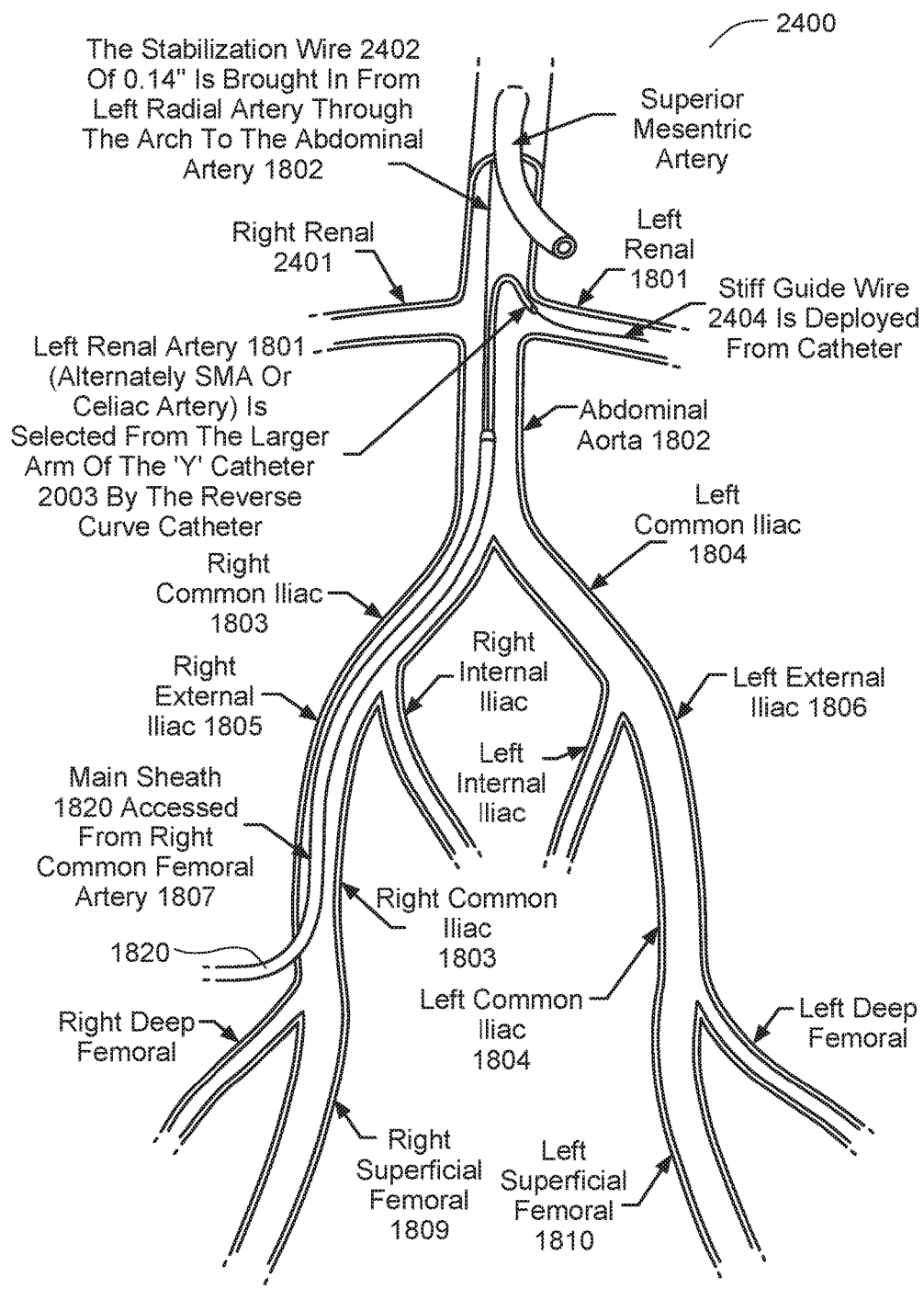
FIG. 25 is a pictorial representation showing the stabilization wire in place and a reverse curve catheter being used to deploy a stiff guide wire into the left renal artery in accordance with one embodiment of the invention.
Figure 26:
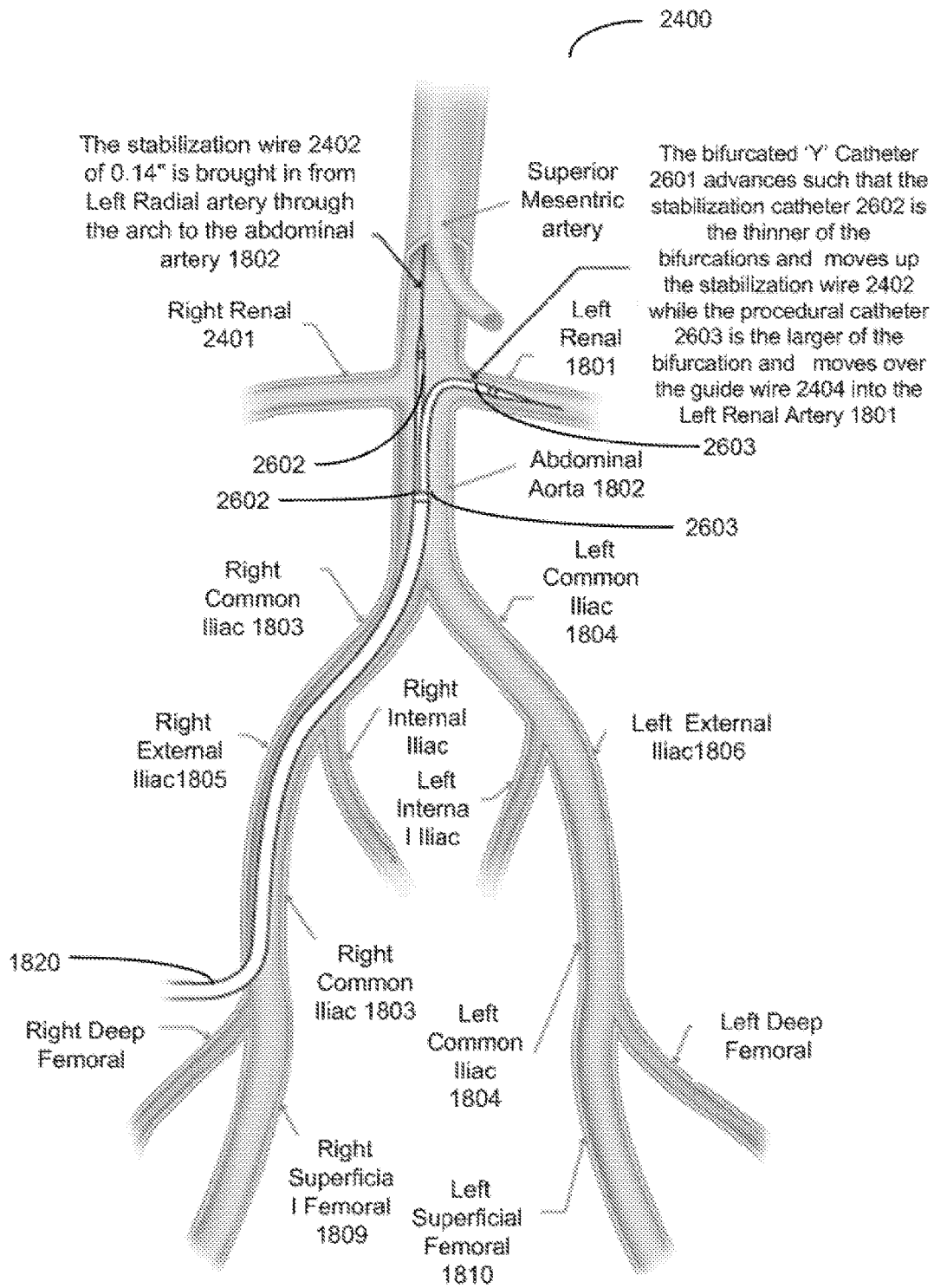
FIG. 26 is a pictorial representation showing the bifurcated catheter extending out of the main sheath with the stabilization wire through the narrow opening/catheter and the procedural catheter along the thick wire from the wider opening in accordance with one embodiment of the invention.
Figure 27:
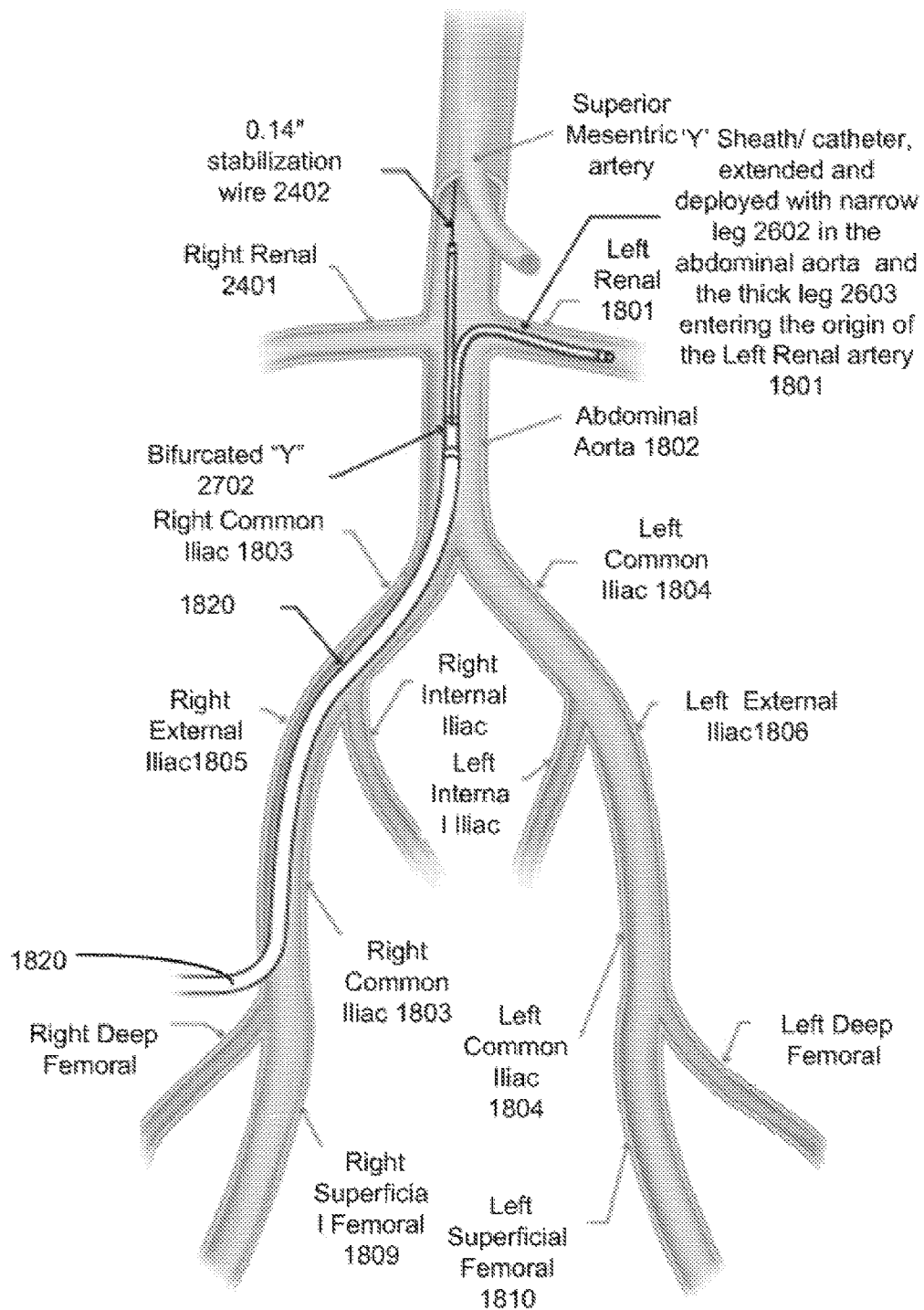
FIG. 27 is a pictorial representation of the stabilized procedural section of the bifurcated catheter ready for visceral interventions in the left renal artery in accordance with one embodiment of the invention.

FIGS. 24-27 illustrate an example of the use of the stabilization technique using bifurcated sheath/catheter for visceral interventions. An intervention in the left renal artery 1801 is shown in these figures. The access of the main catheter 1820 as in the previous case is via the right common femoral artery 1807. The main sheath 1820 is guided up into the abdominal aorta 1802 using the visibility provided by the radio opaque tip 1823. A snare 2003 is introduced through the main sheath 1820 to capture a stabilization wire 2402. The access for the stabilization wire 2402 is from the left radial artery through the aortic arch into the abdominal aorta 1802. FIG. 25 shows the stabilization wire 2402 snared and pulled into the tip of the main sheath, through the sheath and out of the proximal end of the main sheath. A common reverse curve catheter 2501 is used to extent a thick guide wire 2404 into the left renal artery 1801. A version may be created whereby a thin guidewire may also be placed into the renal artery. The reverse curve catheter or any selective renal/visceral catheter is removed leaving the guidewire in place. The bifurcated 'Y' catheter or sheath (Hence forth 'Y' Catheter) is now loaded (outside the main sheath) with the smaller branch of the bifurcated 'Y' catheter advancing over the stabilization wire 2402 while the larger arm of the 'Y'' catheter with its inner dilator is advanced over the thick wire 2404. FIG. 26 shows the bifurcated 'Y' catheter advanced all the way through the main sheath 1820. FIG. 26 shows the smaller branch of the bifurcated catheter (with its inner dilator) advancing over the stabilization wire 2402 with simultaneous advancement of the larger arm of the 'Y' catheter (with its inner dilator) over the thick guide wire 2404. FIG. 27 shows the bifurcated catheter 2702 is extended out of the main catheter 1820 with the smaller or narrow arm 2602 moving up the abdominal aorta along the stabilization wire 2402 and the wider arm 2603 moving further into the left renal artery 1801 ready for any procedure needed after any inner dilators have been removed from the lumens. An inner dilator may not necessarily be needed for the smaller lumen.

In another modification of the embodiment described above, a smaller diameter main sheath may be used. The main bifurcated 'Y' sheath is not preloaded into the main sheath. This allows the use of a 6 French snare catheter through the main sheath lumen to grasp the stabilization wire and pull it all the way out through the proximal end or hub of the sheath. Next a reverse curve or renal/visceral selective catheter is advanced through the sheath and out through the tip to select the left renal artery. A thick guide wire is left in place in the left renal artery and the selective catheter is removed. It should be understood that the 2 wires can each be separately loaded through the appropriate lumen of the 'Y'' catheter. The 'Y' catheter can now be advanced as shown in FIG. 26.

Figure 28:
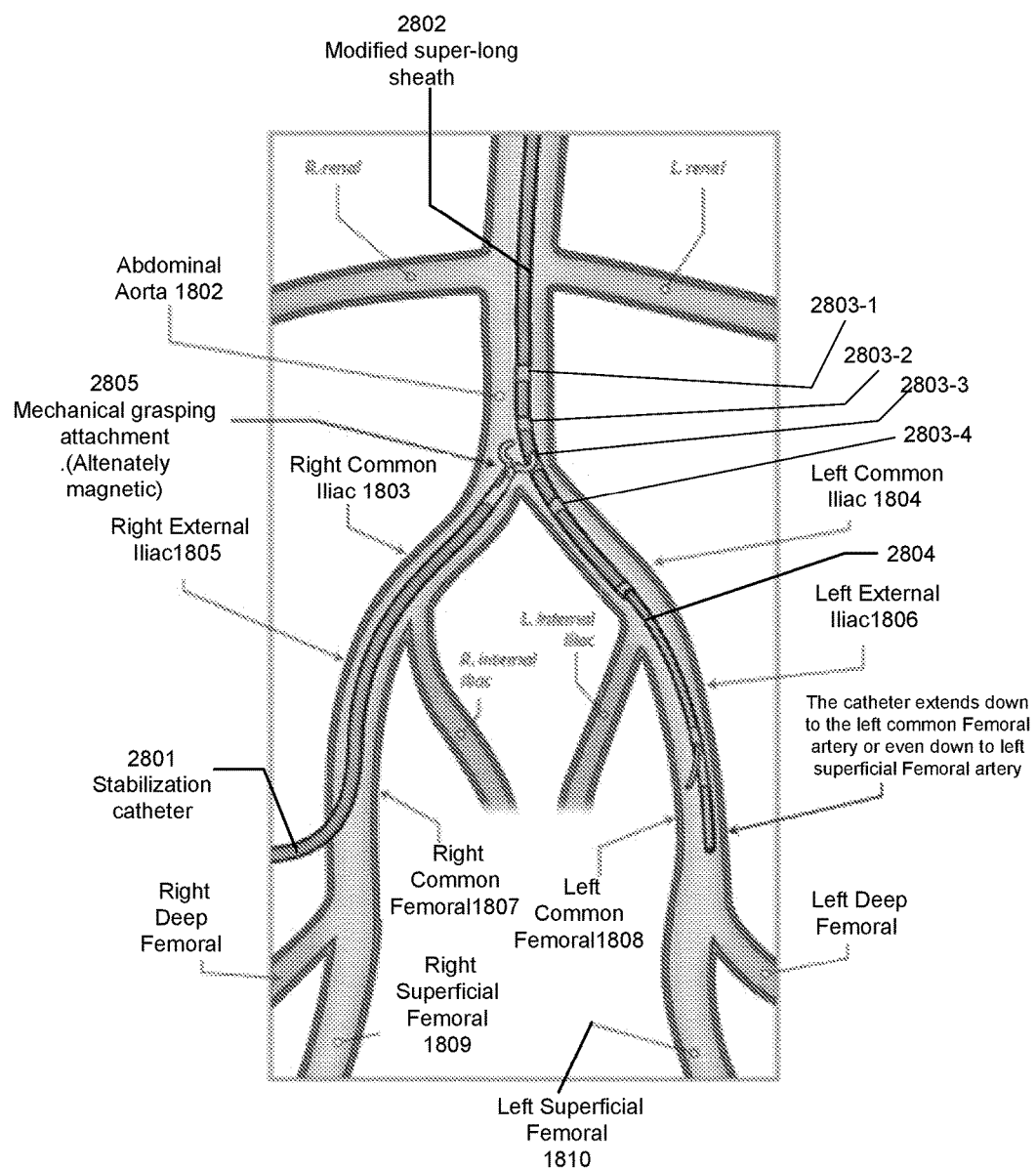
FIG. 28 is a pictorial representation of an antegrade femoral procedure in accordance with one embodiment of the invention.

Another need for stabilization of the procedural catheter or the sheath carrying the procedural catheter is when using very long catheters to reach the location of the procedure. FIG. 28 shows such an application. As is well understood Retrograde, and especially antegrade femoral puncture or access is very difficult in obese patients. Hence a super-long radial artery sheath or super-long sheath that extends to the left common femoral 1808 or the right common femoral 1807 or below-knee arteries such as right superficial femoral 1809 or left superficial femoral 1810 is used for arterial interventions in the femoral artery of these patients. As sheaths become super-long they lack stability and pushablity for common femoral artery and below-knee arterial interventions, especially for chronic total occlusion traversals. In these cases it is possible to provide stabilization and improve the pushability to the super-long sheath carrying the procedural catheter 2804 using the modified super-long sheath like the 2802 with reinforced sections 2803 (2803-1 to 2803-4) and enabling a gripper or grasping attachment 2805 attached to a second stabilization catheter 2801 to attach the second stabilization catheter 2801 to the super-long sheath 2802 to provide stability. FIG. 28 shows the super-long modified sheath 2802 extending down the abdominal aorta 1802 to the left common iliac artery 1804 to the left external iliac 1804. The modified super-long sheath 2802 has reinforced gripper sections 2803-1 to 2803-4. A stabilization catheter 2801, with access from the right common femoral artery 1807 having s a mechanical gripper attachment 2805 at the end is moved up the right common iliac 1803 to make contact with the modified super-long sheath 2802 at the apex of the fork of the iliac arteries and capture one of the reinforced regions such as 2803-3. In an alternate case, the magnetic attachment previously described may be used instead of the mechanical gripper attachment. By capturing and getting attached to the modified super long sheath 2802, the stabilization catheter 2801 is able to enhance the stability and pushability to the modified super long sheath 2802. The procedural catheter 2804 is now able to be extended into the left common and left superficial femoral arteries to conclude procedures. It should be noted that further stabilization methods already disclosed such as side hole stabilization or stabilization using bifurcated Y catheter, or even an additional stabilization by use of a magnetic or mechanical gripper attachment may be used in conjunction with the above, when needed to improve the success of the procedure.

Though the above examples show specific examples with access points for the procedural catheter and the stabilization catheter/wires, it is not meant to be limiting. There may be other scenarios possible for access and stabilization of procedural catheter or sheath depending on the location of the procedure and the nature of the patient. The stabilization schemes proposed using either the bifurcated 'Y' catheter, the bifurcated side hole catheter or the dual catheter and the modified sheath catheter with the latching mechanism, are all usable to provide stability where the procedures are conducted in tortuous branches of major vessels. As is well understood the preferred method will vary based on the location of the procedure and the nature of the patient.

As will be understood by those familiar with the art, the invention may be embodied in other specific forms without departing from the spirit or essential characteristics thereof. Likewise, the particular naming and division of the members, features, attributes, and other aspects are not mandatory or significant, and the mechanisms that implement the invention or its features may have different structural construct, names, and divisions. Accordingly, the disclosure of the invention is intended to be illustrative, but not limiting, of the scope of the invention.

While the invention has been described in terms of several embodiments, those of ordinary skill in the art will recognize that the invention is not limited to the embodiments described, but can be practiced with modification and alteration within the spirit and scope of the appended claims. The description is thus to be regarded as illustrative instead of limiting. There are numerous other variations to different aspects of the invention described above, which in the interest of conciseness have not been provided in detail. Accordingly, other embodiments are within the scope of the claims.

The invention has been described in relation to particular examples, which are intended in all respects to be illustrative rather than restrictive. Those skilled in the art will appreciate that many different combinations will be suitable for practicing the present invention. Other implementations of the invention will be apparent to those skilled in the art from consideration of the specification and practice of the invention disclosed herein. Various aspects and/or components of the described embodiments may be used singly or in any combination. It is intended that the specification and examples be considered as exemplary only, with a true scope and spirit of the invention being indicated by the following claims.

What is claimed is:

1. A method for treating contralateral lower extremity peripheral arterial disease comprising:
    creating a contralateral percutaneous femoral access;
    advancing a guidewire to an abdominal aortic bifurcation from the contralateral percutaneous femoral access to the abdominal aortic bifurcation using radiographic imaging;
    advancing a main sheath catheter over the guidewire to the abdominal aortic bifurcation;
    extending the guidewire through an ipsilateral iliac;
    inserting a bifurcated catheter through the contralateral percutaneous femoral access and guiding it over the guidewire to the abdominal aortic bifurcation, the bifurcated catheter having a proximal end and a bifurcation at its distal end comprising a procedural lumen and a stabilization lumen;
    creating an ipsilateral percutaneous femoral access;
    inserting a stabilization wire through the ipsilateral percutaneous femoral access and guiding it to the abdominal aortic bifurcation;
    advancing a snare wire through the stabilization lumen of the bifurcated catheter to the abdominal aortic bifurcation, wherein the snare wire comprises a proximal end and a distal end that includes a snare;
    using the snare at the distal end of the snare wire to: ensnare the stabilization wire inserted and advanced to the abdominal aortic bifurcation from the ipsilateral percutaneous femoral access, and pull the stabilization wire into the stabilization lumen of the bifurcated catheter to have a distal end of the stabilization wire exit at the proximal end of the bifurcated catheter outside the contralateral percutaneous femoral access; and
    guiding the bifurcated catheter over the guidewire and the stabilization wire, through the ipsilateral iliac to an ipsilateral percutaneous femoral artery such that the stabilization lumen is located at the ipsilateral percutaneous femoral access, the proximal end of the stabilization wire is outside of the ipsilateral percutaneous femoral access, and a distal end of the stabilization wire is outside the contralateral percutaneous femoral access,
    wherein the distal end and the proximal end of the stabilization wire are outside of the ipsilateral percutaneous femoral access and the contralateral percutaneous femoral access, such that the stabilization wire is configured to receive a force applied between the distal end and the proximal end outside the ipsilateral percutaneous femoral access and the contralateral percutaneous femoral access to provide an end-to-end tension, with increased pushability and stability to the bifurcated catheter using the stabilization wire.

2. The method of claim 1, wherein the stabilization lumen is smaller than the procedural lumen.

3. The method of claim 2, further comprising:
    advancing the snare wire out of the stabilization lumen of the bifurcated catheter, snaring the stabilization wire with the snare; and
    pulling the stabilization wire through the bifurcated catheter and out of the contralateral percutaneous femoral access using the snare wire.

4. The method of claim 3, further comprising pulling the stabilization wire through the stabilization lumen to the proximal end of the bifurcated catheter such that the distal end of the stabilization wire is outside the contralateral percutaneous femoral access and the proximal end of the stabilization wire is outside the ipsilateral percutaneous femoral access.

5. The method of claim 4, further comprising applying tension to the stabilization wire by applying pressure at the first and second ends of the stabilization wire.

6. The method of claim 1, further comprising inserting the guidewire, the main sheath catheter, the bifurcated catheter and the snare wire via the contralateral percutaneous femoral access.

7. The method of claim 2, further comprising advancing a reverse curve catheter along the guidewire through the procedural lumen of the bifurcated catheter to the abdominal aortic bifurcation, wherein the reverse curve catheter allows the guidewire to turn into the ipsilateral percutaneous femoral artery at the aortic bifurcation.

8. The method of claim 7, further comprising removing the reverse curve catheter after delivering the guidewire into the ipsilateral percutaneous femoral artery.

9. The method of claim 7, further comprising advancing the bifurcated catheter such that the procedural lumen of the bifurcated catheter advances over the guidewire to a treatment site while the stabilization lumen advances over the stabilization wire to the ipsilateral percutaneous femoral access.

10. The method of claim 9, further comprising removing the guidewire and performing a treatment procedure at the treatment site.

11. The method of claim 7, further comprising advancing the bifurcated catheter into the ipsilateral percutaneous femoral artery from the abdominal aortic bifurcation, wherein the stabilization wire extends through a side hole forming the bifurcation near the distal end of the bifurcated catheter.

12. The method of claim 2, wherein advancing the bifurcated catheter comprises advancing the stabilization lumen over the stabilization wire and advancing the procedural lumen over the guidewire.

13. The method of claim 12, further comprising removing the guidewire and performing a treatment procedure at the treatment site.

14. A percutaneous minimally invasive interventional method for treating lower extremity peripheral arterial disease using a bilateral percutaneous femoral access, the method comprising:

advancing a guidewire to an abdominal aortic bifurcation from a contralateral percutaneous femoral access using radiographic imaging;

advancing a sheath catheter over the guidewire, wherein the sheath catheter is a bifurcated catheter that comprises a distal end and a proximal end, the distal end of the bifurcated catheter comprises a procedural lumen and a stabilization lumen, wherein the stabilization lumen is smaller than the procedural lumen and the guidewire is inserted through the procedural lumen;

inserting a snare wire through the stabilization lumen of the bifurcated catheter to the abdominal aortic bifurcation, wherein the snare wire comprises a distal end that includes a snare;

advancing a stabilization wire having a first end and a second end to the abdominal aortic bifurcation from an ipsilateral percutaneous femoral access at an ipsilateral femoral artery;

ensnaring the stabilization wire using the snare at the distal end of the snare wire;

pulling the first end of the stabilization wire into the stabilization lumen of the bifurcated catheter and out through the contralateral percutaneous femoral access using the snare at the distal end of the snare wire, wherein the first end of the stabilization wire is outside the contralateral percutaneous femoral access and the second end of the stabilization wire is outside the ipsilateral percutaneous femoral access;

inserting and advancing a reverse curve catheter over the guidewire within the procedural lumen of the bifurcated catheter to turn and advance the guidewire through an ipsilateral iliac artery to the ipsilateral femoral artery and to a procedural site;

removing the reverse curve catheter;

guiding the bifurcated catheter over the guidewire and the stabilization wire, wherein the stabilization lumen is positioned at the ipsilateral percutaneous femoral access and the procedural lumen is positioned at an access to the procedural site;

removing the guidewire; and applying a tension to the stabilization wire between the first end and the second end outside the contralateral percutaneous femoral access and the ipsilateral percutaneous femoral access; and locking the stabilization wire in place to provide stabilization and pushability to the procedural lumen of the bifurcated catheter and to any procedural catheter or instruments inserted through the procedural lumen of the bifurcated catheter for a procedure at the procedural site.

* * * * *